US010531798B2

United States Patent
Nanaumi et al.

(10) Patent No.: US 10,531,798 B2
(45) Date of Patent: Jan. 14, 2020

(54) PHOTOACOUSTIC INFORMATION ACQUIRING APPARATUS AND PROCESSING METHOD

(71) Applicant: CANON KABUSHIKI KAISHA, Tokyo (JP)

(72) Inventors: Ryuichi Nanaumi, Tokyo (JP); Takuro Miyasato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 980 days.

(21) Appl. No.: 14/967,497

(22) Filed: Dec. 14, 2015

(65) Prior Publication Data
US 2016/0174849 A1 Jun. 23, 2016

(30) Foreign Application Priority Data

Dec. 22, 2014 (JP) .................................. 2014-259032

(51) Int. Cl.
*A61B 5/00* (2006.01)
*G06T 11/00* (2006.01)
*A61B 8/08* (2006.01)

(52) U.S. Cl.
CPC .......... *A61B 5/0095* (2013.01); *G06T 11/006* (2013.01); *A61B 8/0825* (2013.01); *G06T 2211/421* (2013.01)

(58) Field of Classification Search
CPC ... A61B 5/0095; A61B 8/0825; G06T 11/006; G06T 2211/421
See application file for complete search history.

(56) References Cited

U.S. PATENT DOCUMENTS

| 8,144,327 | B2 | 3/2012 | Nakajima et al. | 356/432 |
|---|---|---|---|---|
| 2006/0159395 | A1* | 7/2006 | Hnatiw | G02B 6/12011 385/37 |
| 2010/0053618 | A1* | 3/2010 | Nakajima | A61B 5/0059 356/432 |
| 2013/0085371 | A1 | 4/2013 | Miyasato | 600/407 |
| 2014/0036636 | A1 | 2/2014 | Miyasato | 367/178 |

(Continued)

OTHER PUBLICATIONS

Hussain et al (Mapping optical fluence variations in highly scattering media by measuring ultrasonically modulated backscattered light; Journal of Biomedical Optics 19(6), 066002 (Jun. 2014.*

(Continued)

*Primary Examiner* — Serkan Akar
(74) *Attorney, Agent, or Firm* — Venable LLP

(57) ABSTRACT

Provided is an object information acquiring apparatus having: a receiving unit receiving an acoustic wave generated from an object, which has been irradiated with light, at a plurality of receiving positions and outputting time-series receiving signals; and a processing unit acquiring characteristic information by back-projecting the receiving signals, and the processing unit includes: a unit acquiring, for each receiving position, a dispersion index of light intensity distribution on a back projection spherical surface; a unit acquiring, for each receiving position, an angle range in the back projection based on the dispersion index; and a unit acquiring the characteristic information by back-projecting the receiving signals in the angle range.

25 Claims, 19 Drawing Sheets

(56) References Cited

U.S. PATENT DOCUMENTS

2015/0238090 A1    8/2015  Suita et al.  .......... A61B 5/0095

OTHER PUBLICATIONS

M. Xu et al., "Universal back-projection algorithm for photoacoustic computed tomography", *Physical Review E*, vol. 71, pp. 016706-1 to 01706-7 (Jan. 19, 2005).
M. Xu et al., "Universal back-projection algorithm for photoacoustic computed tomography", *Physical Review E*, vol. 71, pp. 016706-1 to 016706-7 (Jan. 19, 2005).

* cited by examiner

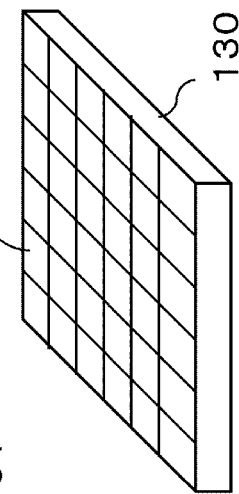
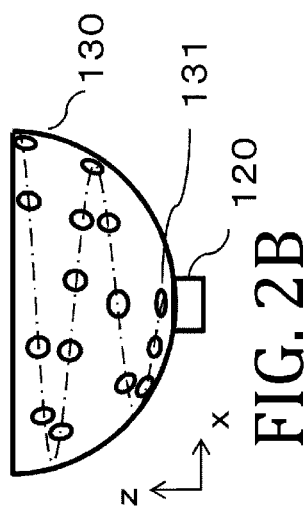
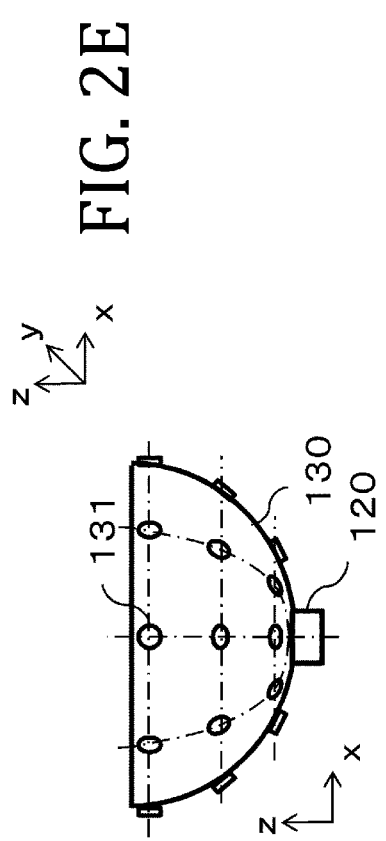
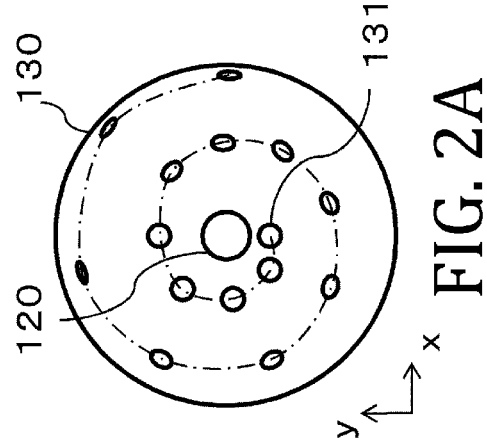
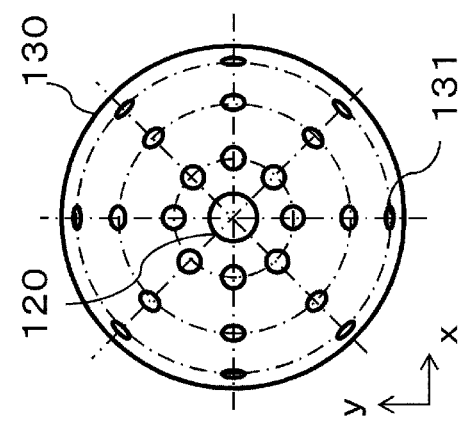

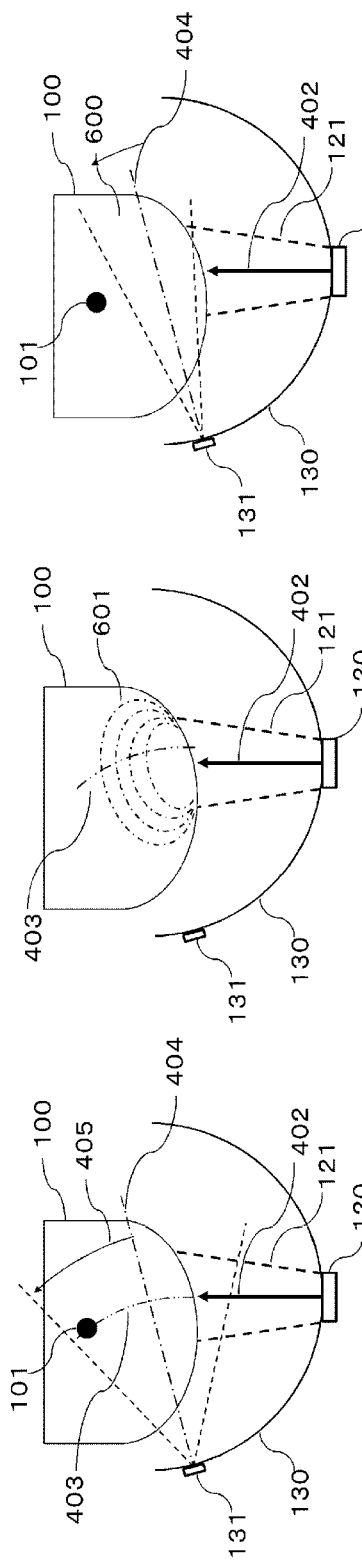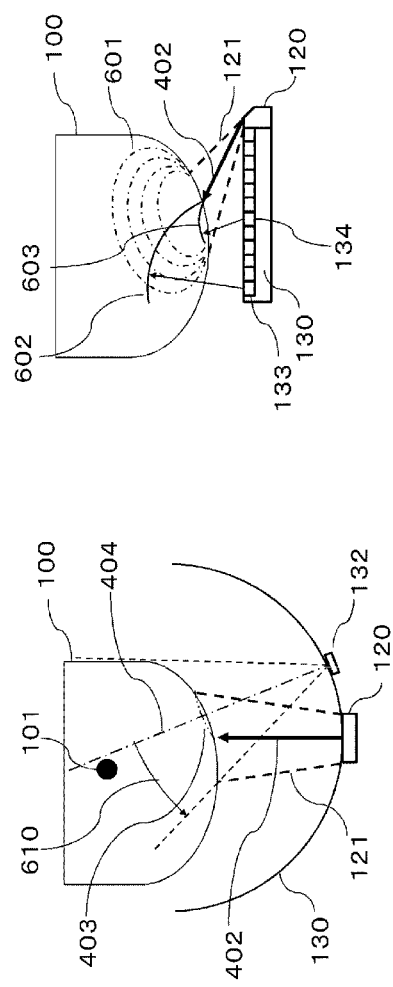

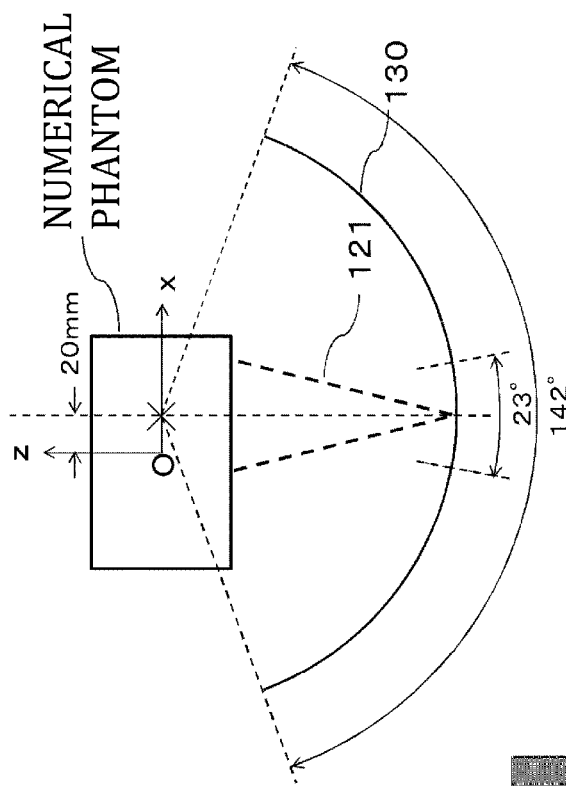
FIG. 8D
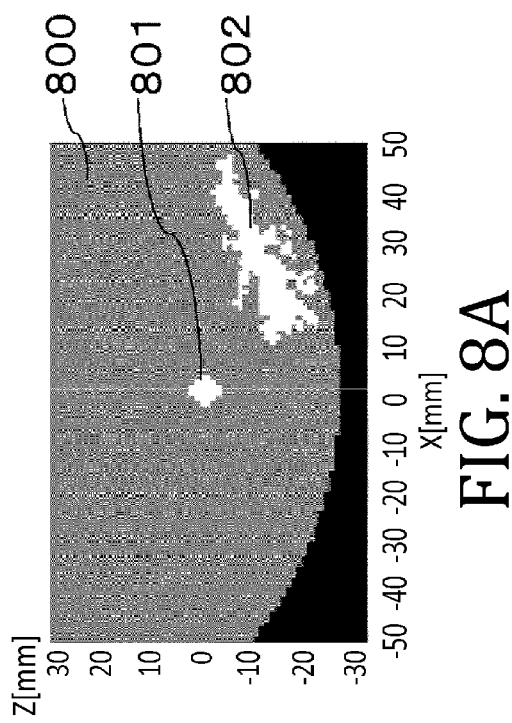
FIG. 8A
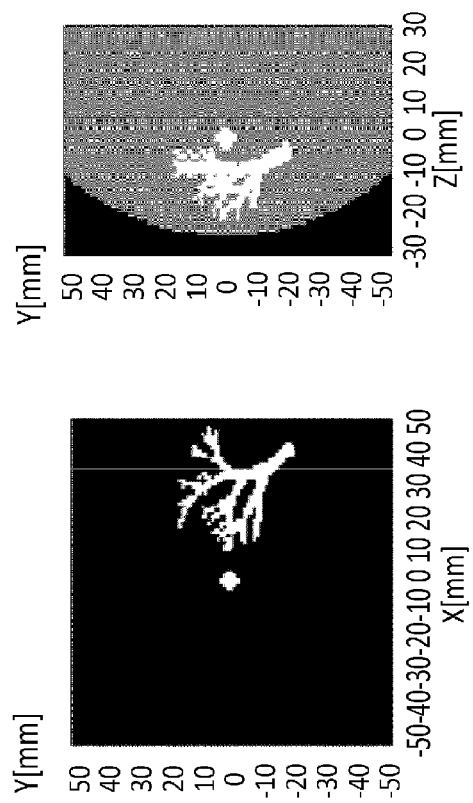
FIG. 8C
FIG. 8B

PHOTOACOUSTIC INFORMATION ACQUIRING APPARATUS AND PROCESSING METHOD

BACKGROUND OF THE INVENTION

Field of the Invention

The present invention relates to an object information acquiring apparatus and a processing method.

Description of the Related Art

As a technique to acquire information on the interior an object, such as a living body, by receiving an acoustic wave, a photoacoustic imaging apparatus, an ultrasonic echo imaging apparatus or the like has been proposed. The photoacoustic imaging apparatus is particularly effective in diagnosing skin cancer and breast cancer, and is expected to replace the ultrasonic echo diagnosis apparatuses, X-ray apparatuses, MRI apparatuses and the like which have been conventionally used.

A photoacoustic imaging apparatus makes information on an object (e.g. living body) visible, utilizing the photoacoustic effect. The photoacoustic effect is a phenomenon where a light absorbing substance (e.g. hemoglobin in blood) inside the object, which is irradiated with visible light, a near infrared or the like, is momentarily expanded by the absorbed light energy, and generates a photoacoustic wave. A tomography technology using this photoacoustic effect is called "photoacoustic tomography".

In photoacoustic imaging, information related to the absorption coefficient inside the object can be imaged. The absorption coefficient is a light energy absorption rate of the tissue of the living body. An example of information related to the absorption coefficient is initial sound pressure, which is sound pressure at the moment when the photoacoustic wave is generated. The initial sound pressure is in proportion to the product of the light energy (light intensity) and the absorption coefficient, hence the absorption coefficient can be calculated based on the initial sound pressure value. Furthermore, the absorption coefficient depends on the concentration of the constituents of the tissue of the living body, hence the concentration of the constituents can be acquired from the absorption coefficient. In particular, the concentration ratio between oxyhemoglobin and deoxyhemoglobin, and the oxygen saturation of the tissue of the living body can be acquired by using the light having a wavelength that can easily be absorbed by hemoglobin in blood. By analyzing the oxygen saturation distribution, tumorous tissue inside the living body and peripheral tissue of the tumor and the like can be identified, therefore photoacoustic imaging is expected to be applied to medical diagnosis.

Minghua Xu and Lihong V. Wang, "Universal back-projection algorithm for photoacoustic computed tomography", PHYSICAL REVIEW E 71, 016706 (2005) discloses a universal back projection (UBP), which is one back projection method, as a method of imaging initial sound pressure from a receiving signal acquired by a transducer, which receives an ultrasonic wave and converts it into an electric signal.

Non Patent Literature 1: Minghua Xu and Lihong V. Wang, "Universal back-projection algorithm for photoacoustic computed tomography", PHYSICAL REVIEW E 71, 016706 (2005)

SUMMARY OF THE INVENTION

A living body, which is a major object of photoacoustic imaging, has a characteristic of scattering and absorbing light. Therefore as light propagates deep into the living body, light intensity decays exponentially. As a result, a strong (high amplitude) photoacoustic wave tends to generate near the surface of the object, and a weak (low amplitude) photoacoustic wave tends to generate in an area deep in the object. Particularly when the object is a breast, a strong photoacoustic wave tends to generate from blood vessels existing near the surface of the object.

In the case of the method according to Minghua Xu and Lihong V. Wang, "Universal back-projection algorithm for photoacoustic computed tomography", PHYSICAL REVIEW E 71, 016706 (2005), when a receiving signal is back-projected to the arc centering around the transducer, a photoacoustic wave having high amplitude near the surface of the object is back-projected to a deep area of the object, and an artifact is generated. Therefore when a tumor or the like, existing in a deep area of the object, is imaged, contrast may drop due to an artifact from the blood vessels on the surface of the object.

With the foregoing in view, it is an object of the present invention to reduce the generation of artifacts in photoacoustic imaging.

The present invention provides an object information acquiring apparatus, comprising:

an irradiating unit configured to irradiate an object with light;

a receiving unit configured to receive an acoustic wave generated from the object, which has been irradiated with the light, at a plurality of receiving positions, and to output time-series receiving signals generated at the plurality of receiving positions respectively; and a processing unit configured to acquire characteristic information on the interior of the object by back-projecting the time-series receiving signals at the plurality of receiving positions, wherein the processing unit comprises:

an index acquiring unit configured to acquire, for each of the plurality of receiving positions, a dispersion index of light intensity distribution on a back projection spherical surface on which the time-series receiving signals is back-projected;

an angle range acquiring unit configured to acquire, for each of the plurality of receiving positions, an angle range to back-project based on the dispersion index; and a characteristic information acquiring unit configured to acquire the characteristic information by back-projecting the plurality of time-series receiving signals in the angle range.

The present invention also provides a processing method performed by an object information acquiring apparatus, having:

an irradiating unit configured to irradiate an object with light;

a receiving unit configured to receive an acoustic wave generated from the object, which has been irradiated with the light, at a plurality of receiving positions, and to output time-series receiving signals generated at the plurality of receiving positions respectively; and a processing unit configured to acquire characteristic information on the interior of the object by back-projecting the time-series receiving signals at the plurality of receiving positions, the method comprising operating the processing unit to execute:

an index acquiring step of acquire, for each of the plurality of receiving positions, a dispersion index of light intensity distribution on a back projection spherical surface for back-projecting the time-series receiving signals;

an angle range acquiring step of acquiring, for each of the plurality of receiving positions, an angle range in the back projection, based on the dispersion index; and a characteristic information acquiring step of acquiring the characteristic information by back-projecting the plurality of time-series receiving signals in the angle range.

And the present invention also provides a non-transitory storage medium storing a program to cause an information processing apparatus to execute a processing method performed by an object information acquiring apparatus, having:

an irradiating unit configured to irradiate an object with light;

a receiving unit configured to receive an acoustic wave generated from the object, which has been irradiated with the light, at a plurality of receiving positions, and to output time-series receiving signals generated at the plurality of receiving positions respectively; and a processing unit configured to acquire characteristic information on the interior of the object by back-projecting the time-series receiving signals at the plurality of receiving positions, the processing unit executing:

an index acquiring step of acquiring, for each of the plurality of receiving positions, a dispersion index of light intensity distribution on a back projection spherical surface for back-projecting the time-series receiving signals;

an angle range acquiring step of acquiring, for each of the plurality of receiving positions, an angle range in the back projection, based on the dispersion index; and a characteristic information acquiring step of acquiring the characteristic information by back-projecting the plurality of time-series receiving signals in the angle range.

According to the present invention, the generation of artifacts can be reduced in photoacoustic imaging.

Further features of the present invention will become apparent from the following description of exemplary embodiments with reference to the attached drawings.

BRIEF DESCRIPTION OF THE DRAWINGS

FIG. 2A to FIG. 2E are diagrams depicting details of a probe in Embodiment 1;

FIG. 6A to FIG. 6E are diagrams depicting back projection of a receiving signal based on Embodiment 1;

FIG. 8A to FIG. 8D are diagrams depicting a calculation model of Example 1;

DESCRIPTION OF THE EMBODIMENTS

Figure 1A:
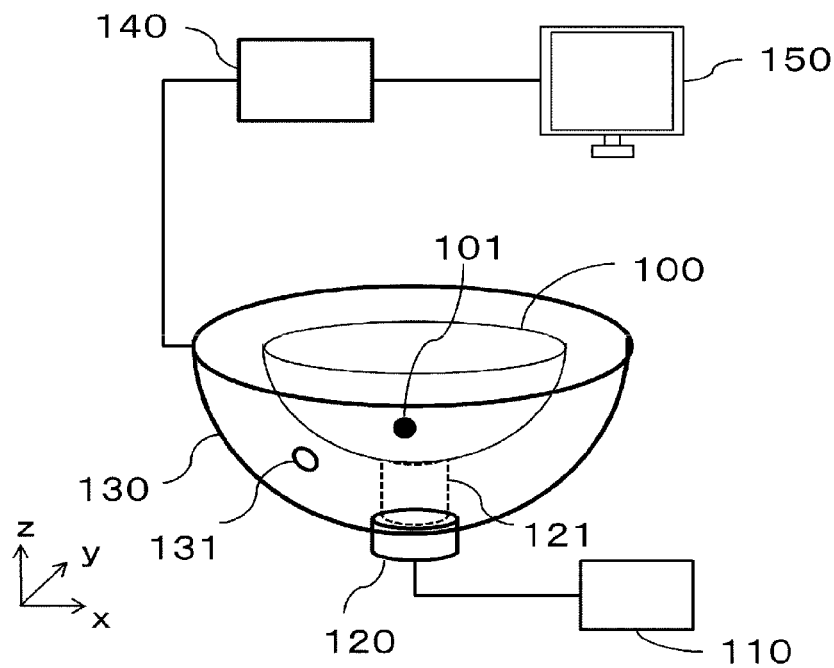
FIG. 1A and FIG. 1B are schematic diagrams depicting an object information acquiring apparatus and a signal processing unit according to Embodiment 1.

Preferred embodiments of the present invention will now be described with reference to the drawings. Dimensions, materials, shapes and relative positions and the like of the components described below should be appropriately changed depending on the configuration and various conditions of an apparatus to which the invention is applied, and are not intended to limit the scope of the invention to the following description.

The present invention is related to a technique to detect an acoustic wave propagated from an object, and generate and acquire characteristic information on the interior the object. Therefore the present invention can be interpreted as an object information acquiring apparatus, a control method thereof, an object information acquiring method, and a signal processing method. The present invention can also be interpreted as a program that allows an information processing apparatus that includes such hardware resources as a CPU to execute these methods, and a storage medium storing this program.

The object information acquiring apparatus of the present invention includes an apparatus using a photoacoustic tomography technique for irradiating an object with light (electromagnetic wave), receiving (detecting) an acoustic wave which is generated at a specific position inside the object or on the surface of the object, and propagating according to the photoacoustic effect. This object information acquiring apparatus can be called a "photoacoustic imaging apparatus" since characteristic information on the interior the object is acquired in the format of image data and the like, based on the photoacoustic measurement.

The characteristic information in the photoacoustic apparatus includes: a generation source distribution of an acoustic wave generated by light irradiation; an initial sound pressure distribution inside the object; a light energy absorption density distribution or an absorption coefficient distribution derived from the initial sound pressure distribution, and a concentration distribution of substance constituting the tissue. In concrete terms, the characteristic information is, for example, an oxy/deoxyhemoglobin concentration distribution, a blood component distribution (e.g. oxygen saturation distribution) determined from the oxy/deoxyhemoglobin concentration distribution, a fat distribution, a collagen distribution or a water distribution. The characteristic information may be determined as distribution information at each position inside the object, instead of numeric data. In other words, the object information can be such distribution information as an absorption coefficient distribution and an oxygen saturation distribution.

The acoustic wave in this invention is typically an ultrasonic wave, and includes an elastic wave that is called a "sound wave" or an "acoustic wave". An acoustic wave generated by the photoacoustic effect is called a "photoacoustic wave" or a "light-induced ultrasonic wave". An electric signal converted from an acoustic wave by a probe is called an "acoustic signal".

[Embodiment 1]

An embodiment of the present invention will be described in detail with reference to the drawings. As a rule, same composing elements are denoted with a same reference symbol, where redundant description is omitted.

<General Configuration of Object Information Acquiring Apparatus>

FIG. 1A is a schematic diagram depicting an object information acquiring apparatus according to this embodiment. Each composing element of the apparatus will now be described. The apparatus has a light source 110, an optical system 120, a probe 130 including a transducer 131, a signal processing unit 140, and a display unit 150. A measurement target is an object 100.

Figure 1B:
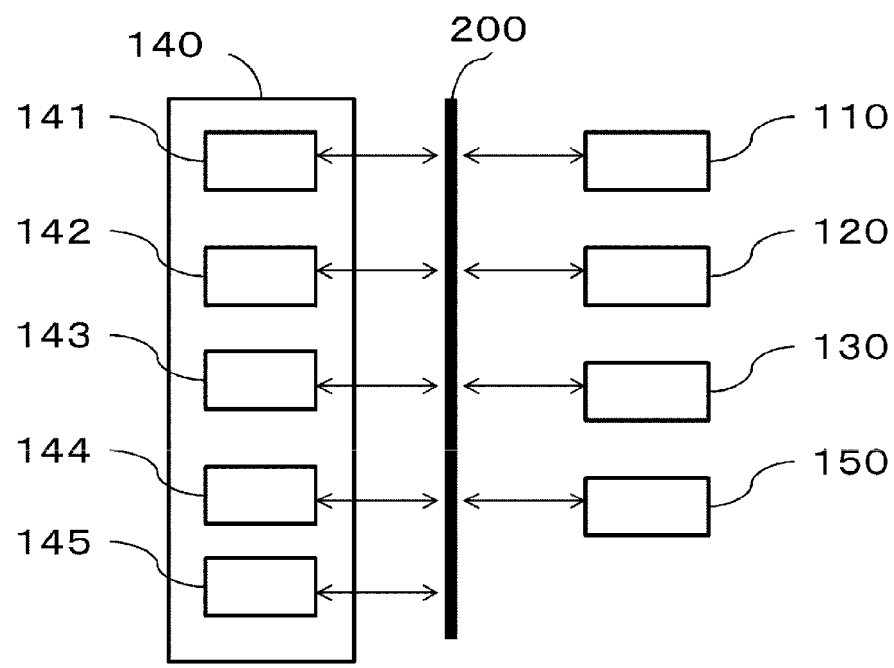

FIG. 1B is a schematic diagram depicting a detailed configuration of the signal processing unit 140, and a configuration around the signal processing unit 140. The signal processing unit 140 includes a control unit 141, a storage unit 142, a light intensity distribution acquiring unit 143, an angle range acquiring unit 144, and an image reconstructing unit 145.

The control unit 141 controls operation of each composing element of the object information acquiring apparatus via a bus 200. The control unit 141 also operates the object information acquiring apparatus according to a program in which the object information acquiring method is written (stored in the storage unit 142), and implements the functions of the light intensity distribution acquiring unit 143, the angle range acquiring unit 144, the image reconstructing unit 145 and the like.

The storage unit 142 stores the program in which the object information acquiring method is written. The storage unit 142 also temporarily stores input/output data from each unit when the imaging operation is performed as the apparatus, and makes data exchange between each unit possible. Each unit may include a data storage unit to perform each processing independently from the storage unit 142. The storage unit 142 may store a specified value of an angle range that can be used for image reconstruction at each of a plurality of receiving positions to receive the acoustic wave from the object.

When the photoacoustic measurement is performed, the light generated by the light source 110 is radiated as a pulsed light 121 to the object 100 via the optical system 120. As a result, an acoustic wave is generated in a light absorber 101 inside the object, or on the surface of the object. The transducer 131 of the probe 130 receives the acoustic wave propagated from the object, converts the acoustic wave into time-series analog electric signals (time-series receiving signals), and outputs the signals.

If the signal processing unit 140 performs UBP by a conventional method using the time-series receiving signals from the transducer 131, an artifact appears in a region of interest including a light absorber 101 due to the acoustic wave generated near the surface of the object. Then the contrast of the light absorber 101 drops since the receiving signals from an area where light intensity is high are back-projected to an area where light intensity is low. Therefore the signal processing unit 140 according to the present invention does not use the receiving signals acquired in an area where the light intensity is high, when a minimal unit (e.g. pixel or voxel) constituting a region of interest is imaged, so as to decrease the generation of artifacts. In concrete terms, the signal processing unit 140 sets an angle range to be used for the image reconstruction, based on the light intensity distribution on a back projection spherical surface centering around the transducer 131.

<Details on Composing Elements>

Details on each composing element of the object information acquiring apparatus according to this embodiment will be described.

(Object 100 and Light Absorber 101)

Neither are part of the object information apparatus of the present invention, but will be described here. The object information acquiring apparatus of the present invention is primarily used for diagnosing, for example, malignant tumors and vascular diseases of humans and animals, and for follow up examination of chemotherapy. Therefore an expected object is a living body, specifically a diagnostic target segment such as a breast, neck and abdomen of a human and animal.

A light absorber existing inside the object is assumed to have a relatively high light absorption coefficient inside the object. For example, if the measurement target is a human body, oxyhemoglobin or deoxyhemoglobin, blood vessels containing considerable oxy/deoxyhemoglobin, or a malignant tumor that includes a considerable number of neovessels, can be the light absorber to be measured. Plaque in a carotid artery wall can also be a measurement target.

To stabilize the shape of the object 100, it is preferable to dispose a holding member having a plate shape, a hemispherical shape or the like. If the shape of the object is stabilized, calculation of the propagation of light inside the object becomes easier, and light quantity in each minimal unit can be more easily determined. It is also advantageous to use a holding member when light quantity for each minimal unit is stored in the storage unit corresponding to the positional relationship between the light irradiation position and the object. The holding member preferably has high transmissivity with respect to light and an acoustic wave, and has a stable shape. In the case of the probe 130 in FIG. 1A, a holding member having a hemispherical shape (or cup or plate shape) is preferable.

(Light Source 110)

For the light source 110, a pulsed light source that can generate a pulsed light in a several nano to several micro second order is preferable. In concrete terms, it is preferable that the light source 110 can generate a light having about a 10 nano second pulse width, in order to generate the photoacoustic wave efficiently. The wavelength of the light generated by the light source 110 is preferably a wavelength by which light can propagate to the inside of the object. In concrete terms, if the object is a living body, a wavelength of 500 nm or more and 1200 nm or less is preferable. To determine the optical characteristic value distribution of a tissue of a living body that exists relatively near the surface of a living body, however, a wavelength range that is wider than the above mentioned wavelength range can be used (e.g. 400 nm to 1600 nm).

For the light source, a laser or light emitting diode can be used. For the laser, various lasers can be used, such as a solid-state laser, gas laser, dye laser and semiconductor laser. For example, an alexandrite layer, a yttrium-aluminium-Garnet laser, a titanium-sapphire laser or the like can be used as the laser.

(Optical System 120)

The light emitted from the light source 110 is shaped to a desired light distribution shape by the optical system 120 including optical components, and is guided to the object 100. The light may be propagated using such an optical wave guide as an optical fiber. The optical components are, for example, a mirror to reflect the light, a lens to collect or magnify light or change the shape of the light, a prism to diffuse, refract or reflect light, an optical fiber to propagate the light, a diffusion plate to diffuse the light and the like. The optical component can be any component as long as the light emitted from the light source 110 can be radiated to the object in a desired shape of the light.

The intensity of light radiated from the optical system 120 to the object 100 may be set and stored in the storage unit 142 in advance. The control unit 141 drives the light source 110 so as to radiate the irradiation light at this intensity. Alternatively, a photosensor may be installed in the light source 110 or the optical system 120 so that the intensity of the irradiation light is determined by measuring a part of the actually emitted light, and stored in the storage unit 142. If the light source 110 itself can emit a desired light in terms of shape, distribution, intensity and the like, the optical system 120 need not be used. The optical system 120, or the light source 110, or a combination thereof corresponds to the irradiating unit of the present invention.

(Probe 130)

The probe 130 includes a transducer 131 and a support member. The transducer 131 is a receiving element that receives a photoacoustic wave, and converts the photoacoustic wave into an electric signal, which is an analog signal. The transducer 131 can be any transducer, using a piezoelectric phenomenon, resonance of light, change of electrostatic capacitance or the like, as long as the photoacoustic wave can be received. The frequency component constituting the photoacoustic wave is typically 100 KHz to 100 MHz. Hence it is preferable that the transducer 131 can detect the frequency in this range.

It is preferable that the probe 130 includes a plurality of transducers 131. Then a photoacoustic wave generated by one radiation of light can be acquired at a plurality of receiving positions, therefore the volume of information used for imaging increases, and image quality improves. However even if the probe includes a single receiving element, a similar effect to a probe that includes multiple receiving elements can be acquired if the receiving element is moved among a plurality of receiving positions using a scanning unit.

If the probe 130 has a hemispherical shape, it is preferable that the measurement target is disposed near the center of a sphere constituted by this hemisphere. In FIG. 1A, an object 100 simulating a breast is disposed inside this hemisphere. Then the information to be acquired increases since the photoacoustic wave from various directions can be received at various receiving positions.

If the probe is constituted by a hemispherical support member in which a plurality of transducers are disposed, a high resolution image can be acquired by setting a high sensitivity region where high receiving sensitivity directions (directional axes) of the respective transducers concentrate. The high sensitivity region can also be set using a spherical crown shape, a spherical zone shape, a plate shape, a bowl shape, a part of an ellipsoid, and a plurality of planes or curved surfaces which are three-dimensionally combined, instead of a hemisphere. The probe 130 may have a two-dimensional plane or a line shape. A probe including a single element may be used with scanning.

FIG. 2 shows diagrams depicting details of the probe 130. FIG. 2A and FIG. 2B show the probe 130 where the transducers 131 are disposed spirally. FIG. 2C and FIG. 2D show the probe 130 where the transducers 131 are disposed radially. FIG. 2A and FIG. 2C are diagrams where the probe 130 is viewed in the z axis direction of FIG. 1A, and FIG. 2B and FIG. 2D are diagrams where the probe 130 is viewed in the y axis direction. In either case, the transducers 131 are disposed on the hemispherical surface of the probe 130, hence the photoacoustic wave generated in the object 100 can be received from various angled directions. Here the transducers 131 are disposed spirally or radially, but the disposition is not limited to this. For example, the transducers 131 may be disposed in a grid pattern on the hemispherical surface.

FIG. 2E shows a plane type probe 130. This is an arrayed probe where the transducers 131 are arrayed on an xy plane. In the case of a plane type probe, the optical system 120 can be disposed next to the probe. In the case of holding the object by pressure using a plate, a wide range of the object can be measured by scanning the two-dimensional arrayed probe on the plate using a scanning unit.

It is preferable to fill the space between the probe 130 and the object with a medium to match acoustic characteristics thereof and for propagating an acoustic wave. The medium preferably allows the acoustic characteristics at the interface of the object 100 and the transducer 131 to match, and has a transmittance of the photoacoustic wave that is as high as possible. For example, acoustic matching material, such as water, matching gel or castor oil, is suitable. The transducer 131 corresponds to the receiving unit of the present invention.

(Signal Processing Unit 140)

The signal processing unit 140 includes a control unit 141, a storage unit 142, a light intensity distribution acquiring unit 143, an angle range acquiring unit 144 and an image reconstructing unit 145, as shown in FIG. 1B. The light intensity distribution acquiring unit 143 corresponds to the index acquiring unit of the present invention, and the angle range acquiring unit 144 corresponds to the angle range acquiring unit of the present invention. The signal processing unit 140, excluding the storage unit 142, is typically constituted by such elements as a CPU, a GPU and an A/D convertor, and such circuits as an FPGA and an ASIC.

The signal processing unit also converts time-series analog electric signals outputted from the transducer 131 into time-series digital signals. The signal processing unit may further include a signal amplifier. The signal processing unit 140 may be constituted by a plurality of elements and circuits, instead of being constituted by one element or one circuit. Furthermore, each processing performed by the object information acquiring method may be executed by any element or circuit. Apparatuses that execute each processing are collectively called the "signal processing unit" according to this embodiment.

The storage unit 142 is typically constituted by a storage medium, such as ROM, RAM or hard disk. The storage unit 142 may be constituted by a plurality of storage media. It is preferable that the signal processing unit 140 is configured to pipe-line process a plurality of signals simultaneously. Thereby the time to acquire the object information can be shortened. Each processing performed in the object information acquiring method may be stored in the storage unit 142 as a program to be executed by the signal processing unit 140. The storage unit 142, to store the program, is typically a non-transitory storage medium.

The signal processing unit 140 and the plurality of transducers 131 may be housed in a same case. The signal processing functions of the signal processing unit may be allotted to a signal processing unit inside the case and a signal processing unit outside the case. In this instance, the signal processing unit disposed inside the case and the signal processing unit disposed outside the case are collectively called the "signal processing unit" according to this embodiment. The signal processing unit 140 corresponds to the processing unit according to the present invention.

(Display Unit 150)

The display unit 150 displays the object information outputted from the signal processing unit 140. The display format can be any format, such as a three-dimensional display of the inside of the object, a two-dimensional tomographic image display, or a numeric display of characteristic information, as long as the format is helpful for diagnosis. Auxiliary information to further help user understanding may also be displayed. For the display unit 150, a liquid crystal display, a plasma display, an organic EL display, FED or the like can be used. The display unit 150 may be provided separately from the object information acquiring apparatus according to this embodiment.

<Object Information Acquiring Method>

Each step of the object information acquiring method according to this embodiment will now be described with reference to FIG. 3. Each step is executed by the control unit 141 which controls the operation of each composing element of the object information acquiring apparatus.

(S110: Step of Radiating Light into Object and Generating Photoacoustic Wave)

The light generated by the light source 110 is radiated, as pulsed light 121, into the object 100 via the optical system 120. Then the pulsed light 121 is absorbed inside the object 100, and a photoacoustic wave is generated by the photoacoustic effect. If a photosensor is installed in the light source 110 or the optical system 120, the measured intensity of the irradiation light is stored in the storage unit 142. Thereby a light intensity distribution, where intensity is strongest on the surface of the object and becomes weaker as the location becomes deeper in the object, is generated.

(S120: Step of Receiving Photoacoustic Wave and Acquiring and Saving Time-Series Receiving Signals)

In this step, the probe 130 receives (detects) the photoacoustic wave and outputs the time-series receiving signals from the transducer 131. The outputted time-series receiving signals are stored in the storage unit 142.

(S130: Step of Acquiring Standard Deviation of Light Intensity Distribution)

((S130-1: Acquiring Light Intensity))

In this step [S130], the index of dispersion of the light intensity distribution on the spherical surface (back projection spherical surface) centering around the transducer 131 is acquired for each transducer 131. An in this step [S130-1], the light intensity distribution acquiring unit 143 acquires the light intensity distribution inside the object 100, that is, the light intensity of each minimal unit (pixel or voxel) when the inside of the object 100 is imaged.

A method that can be used to calculate the light quantity is to numerically solve a transport equation or a diffusion equation to express the behavior of light energy in a medium to absorb or scatter light by: a finite element method; a difference method; a Monte Carlo method or the like. If the shape of the object 100 is simple, the light quantity may be calculated using an analytical solution of the transport equation or the diffusion equation. To simplify the calculation, the shape of the object may be approximated to a simple shape. Particularly when the object is held and fixed by a cup or plate, it is easy to acquire or approximate the shape of the object.

An available method for increasing the accuracy of the light intensity calculation is reading the intensity of the irradiation light stored in the storage unit 142 in S110, and using this intensity for the calculation of the light intensity. Another available method is disposing a unit to acquire a shape of the object, acquiring the shape as data, and reflecting this data in the light intensity calculation. As mentioned later, the shape (particularly the surface profile) of the object can be acquired by using such a method as an imaging unit (e.g. camera), or transmitting/receiving an ultrasonic wave or electromagnetic wave.

In this embodiment, light intensity is determined by computation, but a look up table stored in the storage unit may be referred to, so that necessary values are read based on the light intensity during irradiation, the surface profile of the object, the relative positional relationship of the light irradiation position and the object or the like. In this case as well, the light intensity for each minimal unit can be easily acquired if the shape of the object is fixed.

The transport equation and the diffusion equation require at least two parameters: an absorption coefficient which indicates the light absorption characteristic of the object; and a scattering coefficient which indicates the light scattering characteristics of the object. For these parameters, statistical values related to the age of the testee, typical values of the living body corresponding to the average of the statistical values, and values of the parameters acquired by an apparatus that are different from the apparatus of the present invention, can be used. The light intensity distribution may be calculated in advance using the above mentioned statistical values and typical values, and stored in the storage unit 142 in advance, so that the control unit 141 can acquire the light intensity distribution by reading the data in the storage unit 142.

((S130-2: Acquiring Dispersion Index))

Then the light intensity distribution acquiring unit 143 calculates a dispersion of the light intensity distribution on the back projection spherical surface. In this embodiment, the standard deviation of the light intensity distribution is used as the dispersion index. For the dispersion index, such statistical value as dispersion, standard deviation or difference between the maximum value and minimum value of light intensity, or a kurtosis of the spatial shape of the light intensity distribution, for example, may also be used.

In this embodiment, a logarithm of the light intensity distribution is determined, then the standard deviation is acquired. This process makes the dispersion index used for the later mentioned step S140 a value that indicates how many lower light intensity values exist with reference to a high light intensity value. The light intensity decays exponentially in the depth direction of the object, hence many minimal units on the back projection spherical surface 403 tend to have low light intensity. Therefore the average value of the index is shifted to the higher light intensity side by performing logarithmic compression by taking the logarithm. As a result, a dispersion with respect to a high light intensity value as a reference can be acquired.

Figure 4:
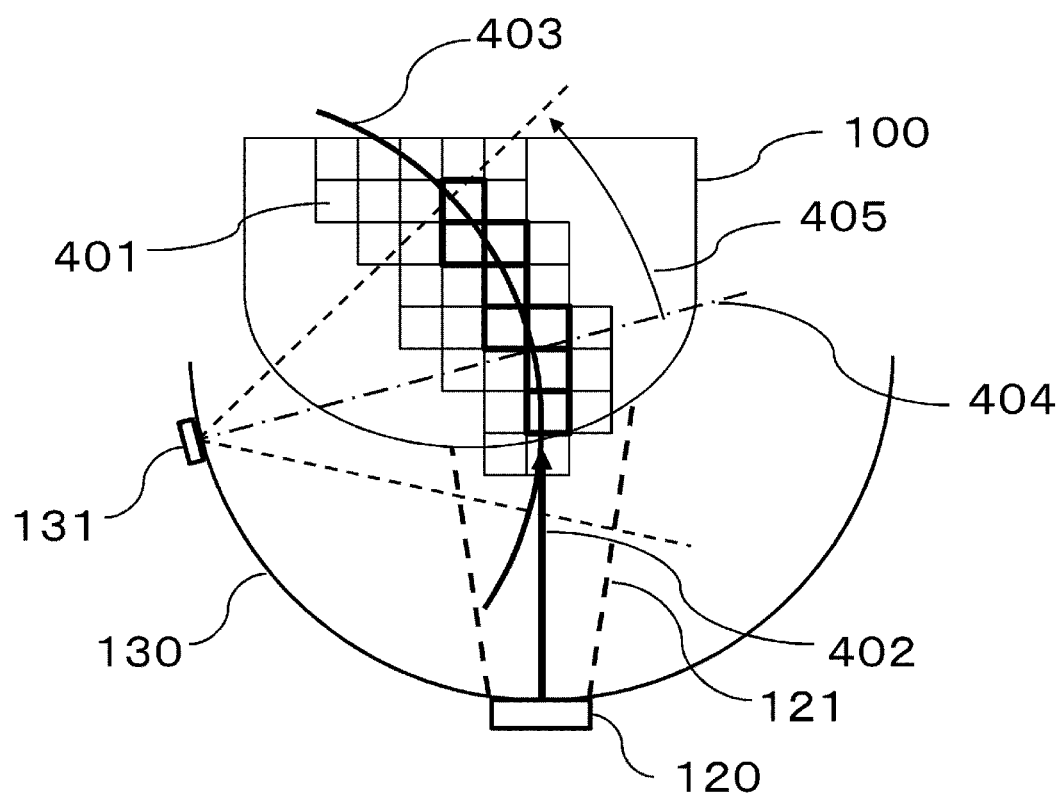
FIG. 4 is a diagram depicting a method for acquiring the index of dispersion of a light intensity distribution.

FIG. 4 is a schematic diagram depicting a region to acquire the standard deviation. The arc indicated by the reference number 403 indicates a portion of the back projection spherical surface centered around the transducer 131. This spherical surface is set so as to include an intersection of the optical axis 402 of the pulsed light and the object 100 (irradiation position). The light intensity distribution acquiring unit 143 calculates the standard deviation using the light intensity of the minimal units existing on the back projection spherical surface 403, out of the minimal units 401 used for imaging the object 100. Further, in this embodiment, minimal units existing within a predetermined angle 405 from the maximum sensitivity direction (directional axis) 404 of the transducer 131 are used, out of the minimal units that exist on the back projection spherical surface 403 and that also exist inside the object 100. Minimal units that satisfy these conditions are highlighted by bold lines.

Normally the maximum sensitivity direction 404 is a direction perpendicular to the receiving surface of the transducer 131, and is also called a "directional axis". The specified angle 405 is arbitrary, and is determined according to the convenience of processing in the later mentioned angle range acquiring step, performance of the transducer, required image accuracy and the like. In this embodiment, the predetermined angle 405 is the range where the receiving intensity is within 50% of the value in the maximum sensitivity direction 404. In the case of three-dimensional measurement, the region included in the predetermined angle 405 becomes a cone of which rotation axis is the maximum sensitivity direction 404 and vertical angle is the predetermined angle 405. The light intensity distribution acquiring unit 143 performs the statistical processing for the light intensity values of the plurality of minimal units that satisfy the above conditions, acquires the standard deviation for each transducer 131, and stores the acquired standard deviation in the storage unit 142.

(S140: Step of Acquiring Angle Range)

In this step, the angle range acquiring unit 144 acquires the angle range to back-project the receiving signals for each of the transducers 131 using the standard deviation acquired in S130. In concrete terms, the angle range becomes smaller as the standard deviation of the transducer becomes greater.

Figure 5A:
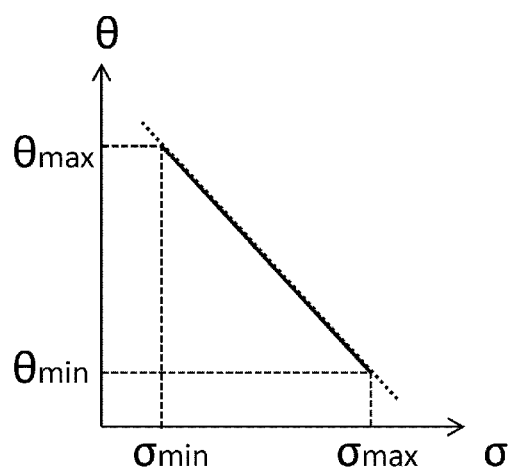
FIG. 5A and FIG. 5B are graphs showing the relationship between the standard deviation and the angle range.
Figure 5B:
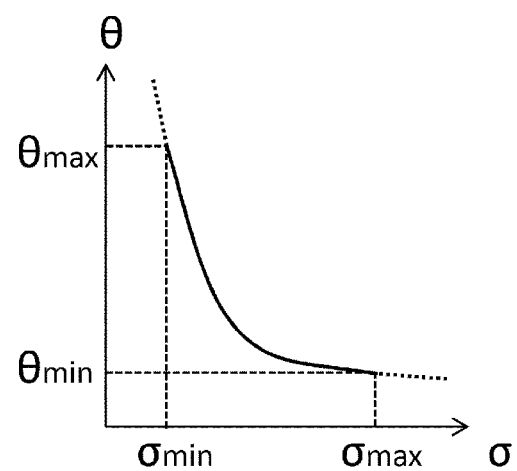

FIG. 5 shows a method for acquiring the angle range θ from the standard deviation σ of the light intensity. FIG. 5A is a case when θ linearly decays with respect to σ, and FIG. 5B is a case when θ decays exponentially with respect to σ. $\sigma_{min}$ and $\sigma_{max}$ are the minimum value and the maximum value of the standard deviation of the plurality of transducers 131 respectively. $\theta_{min}$ and $\theta_{max}$ are the lower limit and the upper limit of the angle range respectively, and can be set to arbitrary values. For example, $\theta_{max}$ can be the predetermined angle 405, and θmin can be an angle sufficiently smaller than the predetermined angle 405.

The processing of this embodiment may be executed for a plurality of times while changing the values of $\theta_{min}$ and $\theta_{max}$, and an image having the best image quality (e.g. contrast) among the acquired plurality of images may be selected. It is preferable that the correspondence shown in FIG. 13 is stored in the storage unit in a format of a mathematical expression, table or the like. In this case, if a plurality of correspondences of which conditions are slightly different from each other is set, the above selection becomes easier. It is preferable that in actual correspondence, the predetermined values are set in advance based on the characteristics of the object, performance of the light source, optical system and transducers, and their positional relationship with the object. It is preferable to set the correspondence unique to the apparatus based on the physical configuration of the apparatus.

FIG. 5 is an example, and any function may be used if the inclination of θ with respect to σ is always 0 or less, and the inclination becomes negative at least once in a range of ($\sigma_{min}$, $\sigma_{max}$). Thereby the angle range for back projection becomes smaller as the transducer has a larger dispersion of light intensity on the back projection spherical surface. Other examples of the function are: the power function shown in FIG. 13A; and the cosine function shown in FIG. 13B. A step function and the like whereby a different angle is applied in steps for each numeric range may be used. In this case, the function includes at least one threshold, and θ decreases in steps as the value of σ increases and exceeds a predetermined threshold. The angle range acquiring unit 144 can acquire θ by, for example, an operation using mathematical expressions or by referring to the table stored in the storage unit.

The above processing is performed for each transducer 131, and an angle range for back-projecting each receiving signal is acquired and stored in the storage unit 142.

(S150: Step of Acquiring Initial Sound Pressure)

In this step, the image reconstructing unit 145 calculates the initial sound pressure distribution inside the object 100. If the region of interest includes a plurality of imaging minimal units (e.g. voxel), the initial sound pressure for each minimal unit, that is, the initial sound pressure distribution in the region of interest, is calculated.

In this embodiment, the Universal Back Projection method expressed by Expression (1) is used as the initial sound pressure calculation method.

[Math. 1]

$$p_0(r_0) = \frac{\sum_i^N b\left(r_i, t = \frac{|r_i - r_0|}{c}\right) \cdot \Delta\Omega_i}{\sum_i^N \Delta\Omega_i} \quad (1)$$

$$b(r_i, t) = 2p(r_i, t) - 2t\frac{\partial p(r_i, t)}{\partial t}$$

Here $r_0$ denotes a position vector which indicates the position to be imaged, $p_0$ ($r_0$, t) denotes an initial sound pressure at the position to be imaged, and c denotes a sound speed of the object 100. $\Delta\Omega i$ is a solid angle of the i-th transducer 131 from the position to be imaged, and N denotes a number of transducers 131 used for imaging.

Expression (1) indicates that time-series receiving signals p ($r_i$,t) are processed (e.g. differentiation), and the results are weighted with a solid angle, and phased and added. Viewed from the transducer 131 side, this processing back-projects (adds) a value of a receiving signal at a certain time to the minimal units of the object 100 belonging to a spherical surface, of which radius is a distance determined by multiplying this time by the sound speed of the object 100. In this embodiment, the receiving signal is back-projected to the minimal units belonging to the spherical surface that each transducer 131 projects with the angle range, which is different for each transducer 131 and acquired in S140, as the vertical angle. In this way, the initial sound pressure distribution inside the object is acquired and stored in the storage unit 142.

The image reconstruction of the present invention is not limited to the above method using Expression (1). Any time domain method that uses the time-series receiving signals of each transducer and the sound speed of the photoacoustic wave inside the object, out of the methods for determining the initial sound pressure for each minimal unit based on the receiving signal intensity at the plurality of receiving positions, can be used in the present invention.

Now it will be described that acquiring the initial sound pressure distribution like this can reduce artifacts. FIG. 6A shows a prior art in which the transducer 131 back-projects the receiving signal in the angle range of the predetermined angle 405. FIG. 6B shows a general light intensity distribution inside the object 100. The reference number 601 indicates the contour line of the light intensity. The light intensity is highest on the surface of the object, and decays exponentially as the location becomes deeper in the object. If the back projection spherical surface 403 in FIG. 6A and the light intensity distribution in FIG. 6B are superimposed, it is known that the receiving signal having high intensity, originating from a photoacoustic wave generated on the surface of the object, is back-projected to a region, which is located deeper in the object and has weak light intensity, and generates artifacts.

FIG. 6C shows the state of back projection according to this embodiment. The angle range 600 in FIG. 6C is acquired based on the dispersion of the light intensity distribution on the back projection spherical surface 403, which is smaller than the angle 405 in FIG. 6A. This is because the light intensity dispersion index on the back projection spherical surface 403 is large. Therefore the influence of the receiving signal originating from the surface of the object on the back projection is suppressed, and the generation of artifacts can be reduced as a result.

FIG. 6D shows another transducer 132. If FIG. 6D and FIG. 6B are superimposed, it is known that the inclination of light intensity in the back projection spherical surface 403 in FIG. 6D is relatively gentle. In other words, unlike the transducer 131, the transducer 132 is less likely to generate an artifact in the deep areas of the object, hence the transducer 132 back-projects the receiving signal in an angle range 610, which is larger than the angle range 600. By adaptively changing the angle range like this, artifacts can be reduced, while preventing the situation where the initial sound pressure of the light absorber 101 cannot be calculated (cannot be imaged) by uniformly decreasing the angle range.

FIG. 6E shows a case when a plane type probe 130 is used. The transducer 133 back-projects the receiving signal to the back projection spherical surface 602 in the direction where the light intensity decays exponentially, and the transducer 134 back-projects the receiving signal to the back projection spherical surface 603 in a direction where the light intensity changes gently. Therefore according to this embodiment, even if the plane probe is used, a similar effect as the case of the above mentioned spherical probe can be implemented. Even in the case of a single element or linear arrayed elements, the angle range to be used for appropriate image reconstruction can be determined according to the shape of the object, irradiation intensity, light intensity distribution inside the object based on the positional relationship between the light irradiation position and the object, and the positional relationship of the element(s) and the object.

Figure 7:
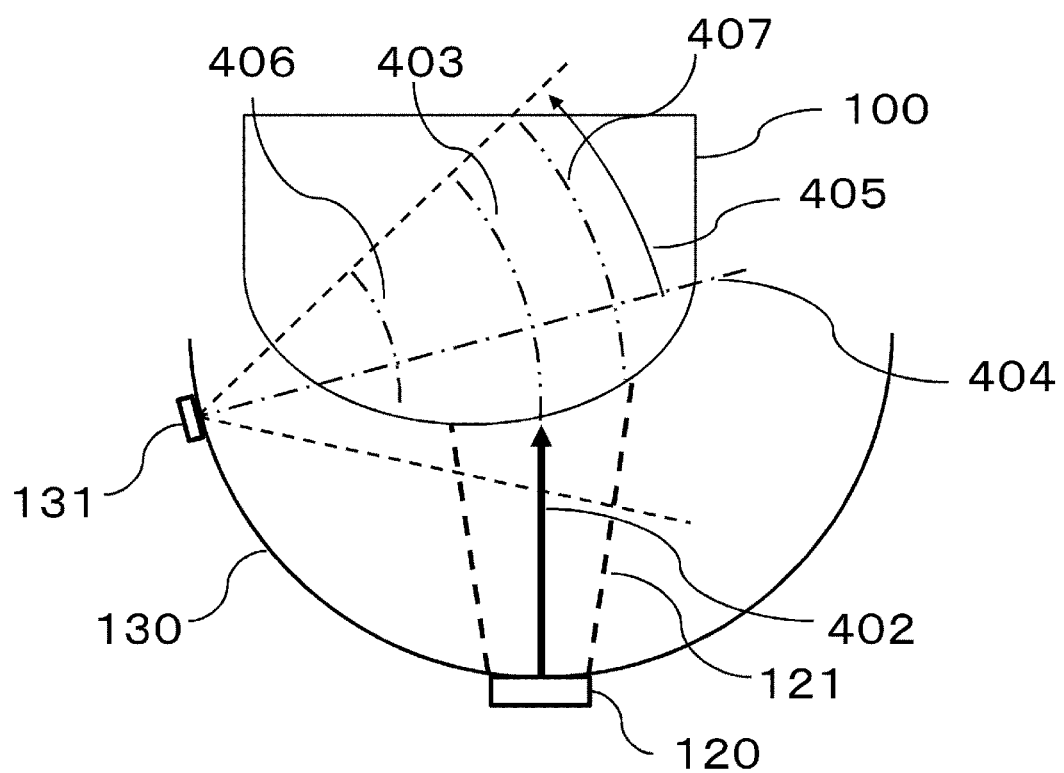
FIG. 7 is a diagram depicting a plurality of back projection spherical surfaces.

The angle range may be acquired for each of a plurality of back projection spherical surfaces having a different radius and corresponding to the signal value of the time-series receive signals at each timing. In other words, as shown in FIG. 7, the dispersion index of the light intensity distribution is acquired on each back projection spherical surface indicated by the reference numbers 406 and 407, and the angle range is individually set. Thereby a more appropriate angle range for each back projection spherical surface can be set, and as a consequence, the effect of this embodiment can be further enhanced.

(S160: Step of Displaying Object Information)

In this step, the object information of the region of interest is displayed on the display unit 150 using the initial sound pressure distribution, which is acquired and stored in the storage unit 142 in S150. For the object information, the initial sound pressure distribution, an absorption coefficient distribution, an oxygen saturation or the like can be displayed. To display the absorption coefficient distribution, the oxygen saturation or the like, the signal processing unit 140 performs operation for the initial sound pressures distribution, and acquires desired information. The object information displayed on the display unit 150 is information in which artifacts are reduced while maintaining quantitativity, which is appropriate information for an operator, such as a physician, to use for diagnosis.

As described above, according to the object information acquiring method of this embodiment, object information which has high quantitativity with reduced artifacts can be acquired.

<Example 1>

Now the result of simulating the object information acquiring method according to Embodiment 1 will be described.

It is assumed that a calculation model (numerical phantom) shown in FIG. 8 is used. FIG. 8A, FIG. 8B and FIG. 8C are an XZ plane maximum intensity projection (MIP), an XY plane MIP and a ZX plane MIP of the numerical phantom respectively. The size of the numerical phantom is x: 100 mm, y: 100 mm and z: 60 mm. The origin of the coordinate system is the center of the phantom. The numerical phantom is constituted by an object 800, a light absorber 801 and surface blood vessels 802. The object 800 has a spherical surface of which center is (x, y, z)=(0, 0, 60) and radius is 85 mm. The object 800 has optical characteristic values equivalent to a living body at a near infrared wavelength, which are the absorption coefficient $\mu_a$=0.008/mm and scattering coefficient $\mu_s'$=1/mm. The light absorber 801 is a sphere of which center is the origin and diameter is φ5 mm, and has the absorption coefficient $\mu_a$ of blood=0.2/mm at a near infrared wavelength. The surface blood vessels 802 exist near the spherical surface of the object 800, and has the absorption coefficient $\mu_a$=0.2/mm. The light absorber 801 and the surface blood vessels 802 have thermo-mechanical characteristic values equivalent to those of a living body and the Grüneisen coefficient Γ=0.2. Therefore the sound pressure (unit: Pa) of P=$\mu_a$×Γ×(light intensity) is generated and propagated from the light absorber 801 and the surface blood vessels 802.

FIG. 8D shows the positional relationship of the numerical phantom, the probe 130 and the pulsed light 121. The probe 130 is a spherical surface, of which center is (x, y, z)=(20 mm, 0 mm, 0 mm) and radius is 127 mm. Here the cross-sectional view of a two-dimensional plane (y=0) is shown to simplify description, but the probe 130 is actually a three-dimensional system that extends in a direction perpendicular to the page face. The transducers 131 are not illustrated, but 1024 transducers are equally distributed in the angle range of 23° to 142° on both sides on the spherical surface shown in FIG. 8D. A Fibonacci spiral is used to calculate the equal distribution. The pulsed light 121 is radiated vertically from the bottom surface of the probe 130 upwards, and equally irradiates a 5 cm×5 cm region on the surface of the numerical phantom.

The light diffusion equation is used to calculate the light intensity inside the object 800. At this time, the analysis solution waveform of the photoacoustic wave is propagated from the sound source to the transducer 131 using the Green's function of the wave equation, and the result is used as the receiving signal. The sound speed is 1480 m/s throughout the calculation space.

The initial sound pressure distribution is acquired by the UBP method of Expression (1), using the light intensity inside the object 800 and the receiving signal of each transducer acquired like this. In Embodiment 1, the standard deviation is acquired after determining the logarithm of the light intensity. When the angle range is acquired from the standard deviation, the linear function shown in FIG. 5A is used, and the angle range ([$\theta_{min}$, $\theta_{max}$] in FIG. 5A) is 5° to 40°.

Figure 9A:
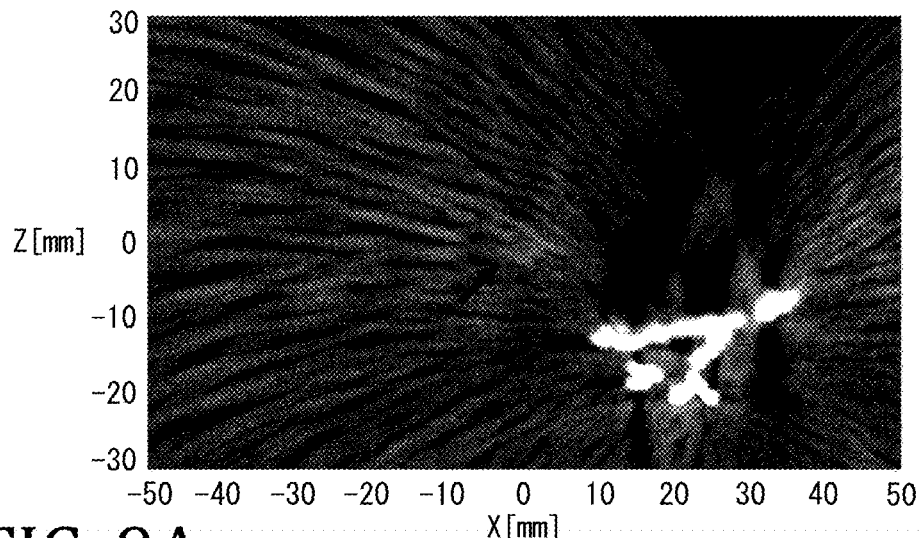
FIG. 9A to FIG. 9C show an effect of Example 1.
Figure 9B:
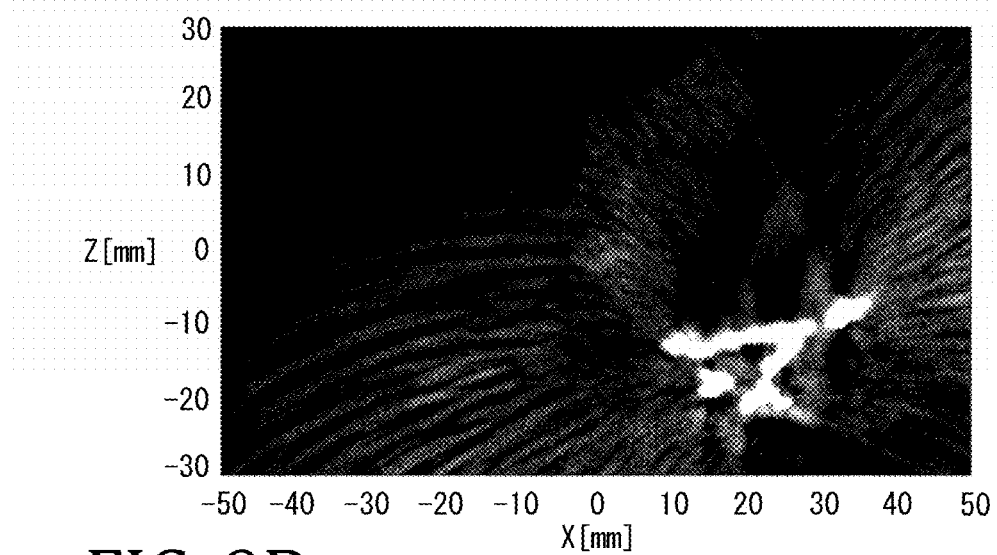

The effect of the present invention in this example will be described with reference to FIG. 9. FIG. 9 shows a result of the simulation performed on the numerical phantom in FIG. 8. FIG. 9A shows the initial sound pressure distribution of a comparative example when the angle range to back-project the signal is fixed to 40°. FIG. 9B is the initial sound pressure distribution when the object information acquiring method of Embodiment 1 is applied. In both FIG. 9A and FIG. 9B, MIP is determined for four slices before and after y=0 (a total of eight slices), and the range of the brightness values is the same. The pitch of the voxel (minimal unit), which is the interval of the slices, is 0.25 mm.

Comparing [FIG. 9A and FIG. 9B], artifacts are reduced and the contrast of a light absorber is improved in FIG. 9B, in the portion indicated by the white arrow mark, for example, showing an improvement in the image quality.

Figure 9C:
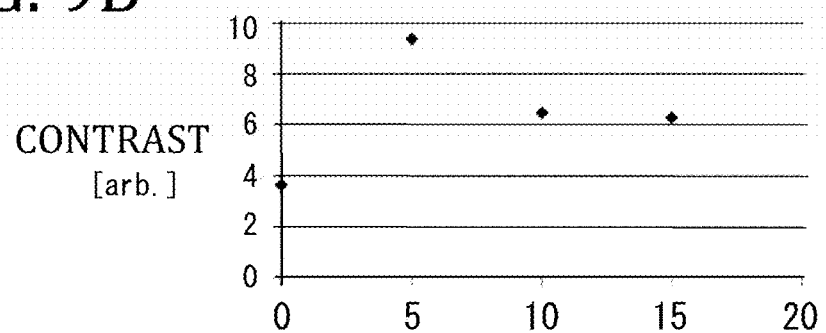

FIG. 9C is a graph of the plurality of images acquired with changing $\theta_{min}$ (0°, 5°, 10° and 15°), where the abscissa indicates $\theta_{min}$, and the ordinate indicates the contrast of the light absorber. The contrast is a ratio of the mean-square value of the brightness values in a region having the diameter φ20 mm surrounding the light absorber excluding the φ5 mm region of the light absorber, with respect to the mean value of the positive brightness values of the minimal units inside the light absorber. According to FIG. 9C, the contrast is highest when $\theta_{min}$ is 5°, hence $\theta_{min}$=5° is set in this example. However the value of $\theta_{min}$ is not limited to 5°. In other words, an optimal $\theta_{min}$ (and/or $\theta_{max}$) can be acquired for each object or for each measurement system using, for example, a method of generating an image a plurality of times while changing $\theta_{min}$ (and/or $\theta_{max}$), and selecting an image having the best image quality (e.g. contrast).

As described above, object information with reduced artifacts can be acquired by using Embodiment 1.

[Embodiment 2]

In this embodiment, an object information acquiring apparatus that can acquire an angle range for back projection with less calculation load compared with Embodiment 1 will be described. As a rule, a composing element the same as Embodiment 1 is denoted with the same reference symbol, for which description is omitted.

<Configuration of Object Information Acquiring Apparatus>

Figure 10A:
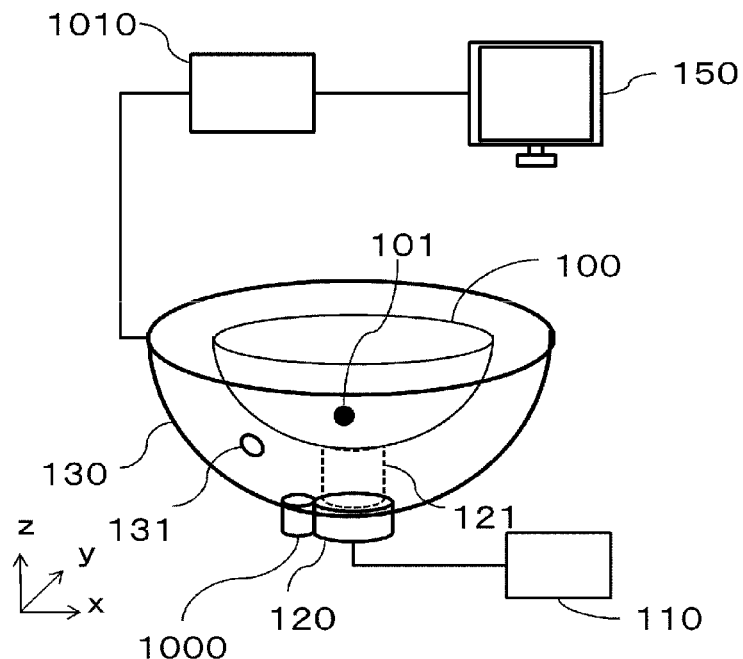
FIG. 10A and FIG. 10B are schematic diagrams depicting an object information acquiring apparatus and a signal processing unit according to Embodiment 2.

FIG. 10A is a schematic diagram of the object information acquiring apparatus according to this embodiment.

(Shape Measurement Camera 1000)

Reference number 1000 denotes a shape measurement camera. This camera acquires the coordinate values of the representative points on the surface of an object 100, and stores the coordinate values in the storage unit 142 as the shape data. A mathematical expression to interpolate the coordinate values of the representative points to determine the shape may be calculated, and the result may be regarded as the shape data. For the shape measurement camera 1000, a depth measurement camera that measures the shape data using the time from irradiation of the measurement light to an object to the return of the reflected light may be used. A general photographing camera to image visible light can also be used. In this case, a plane image of the object 100 is photographed in a plurality of different directions, and the shape data is acquired from these images using a volume intersection method or the like. In the case of using a photographing camera, it is preferable that a plurality of photographing cameras are disposed.

It is preferable that the shape measurement camera 1000 can measure the entire object 100. For example, if the probe 130 and the shape measurement camera 1000 are integrated as shown in FIG. 10A, a scanning mechanism may be disposed in the probe 130 so as to measure the shape by moving the shape measurement camera. The shape measurement camera 1000 may be disposed independently from the probe 130, and a mechanism to retract the probe 130 when the shape is measured must be installed so as to acquire the shape data of the object 100. The shape measurement camera 1000 corresponds to the shape acquiring unit of the present invention.

Shape data may be stored in the storage unit 142 in advance. For example, a holding member to specify and hold a shape of the object 100 is set, whereby the shape data of this holding member is measured in advance, and stored in the storage unit 142. In this case, the shape measurement camera 1000 and the step of acquiring the shape data of the object 100 can be omitted, hence the apparatus configuration can be simplified, and measurement time can be shortened. If the holding member can be replaced depending on the size of the object, the shape data should be stored for each holding member. The holding member corresponds to the holding unit of the present invention.

(Signal Processing Unit 1010)

Figure 10B:
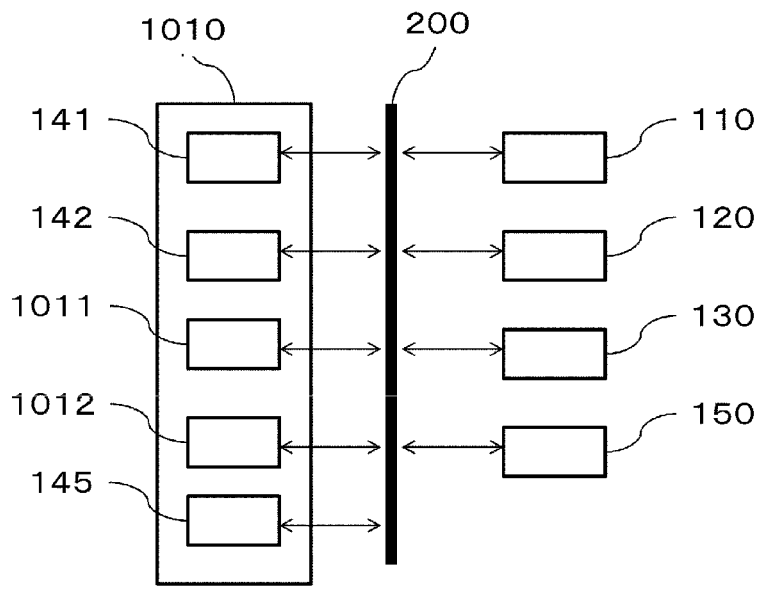

FIG. 10B is a schematic diagram depicting details of the signal processing unit 1010 and the configuration around the signal processing unit 1010. A difference of the signal processing unit 1010 from the configuration of Embodiment 1 is that a relative angle acquiring unit 1011 and an angle range acquiring unit 1012 are included in this embodiment. The relative angle acquiring unit 1011 corresponds to the index acquiring unit of the present invention, and the angle range acquiring unit 1012 corresponds to the angle range acquiring unit of the present invention.

<Object Information Acquiring Method>

Figure 11:
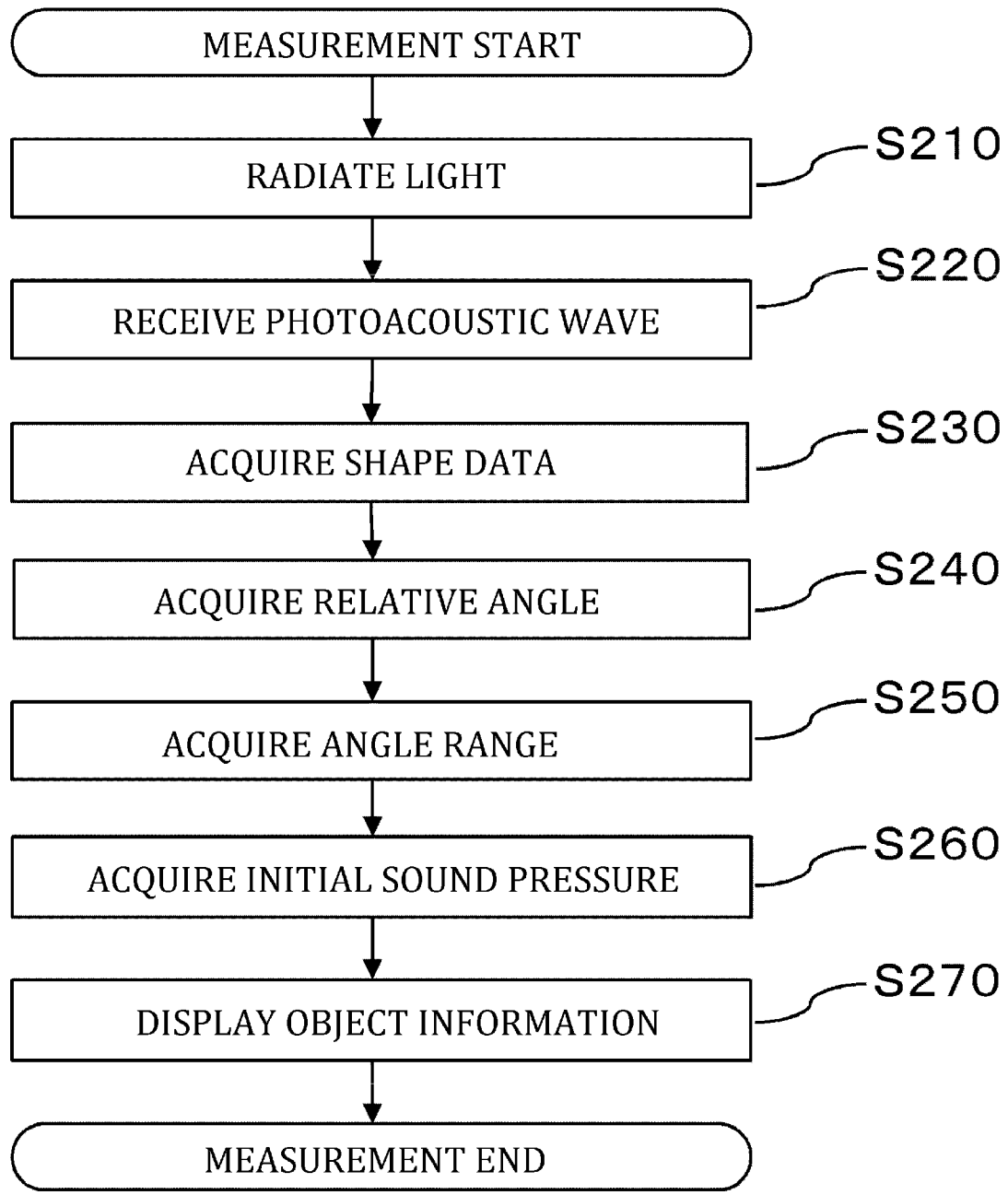
FIG. 11 is a flow chart depicting an object information acquiring method according to Embodiment 2.

Each step of the object information acquiring method according to this embodiment will now be described with reference to FIG. 11. Each step is executed by the control unit 141 which controls operation of each composing element of the object information acquiring apparatus. S210, S220, S260 and S270 in FIG. 11 are the same as S110, S120, S150 and S160 in FIG. 3 respectively, and description thereof is omitted.

(S230: Step of Acquiring Shape Data)

In this step, the shape data of the object 100 is acquired. The shape data may be acquired using the shape measurement camera, or may be acquired by reading the pre-acquired shape data of the holding member from the storage unit 142.

(S240: Step of Acquiring Relative Angle)

In this step, the relative angle acquiring unit 1011 acquires a relative angle for each transducer 131. The relative angle will be described with reference to FIG. 12. The relative angle is an angle formed by a tangential plane 1200 at an intersection between the optical axis 402 of the pulsed light 121 and the object 100, and a line 1210 connecting the transducer 131 and this intersection, and is indicated by the reference number 1220.

First the relative angle acquiring unit 1011 reads the shape data, which was acquired in S230, from the storage unit 142, and calculates the coordinates of the intersection between the optical axis 402 and the object 100. Then the relative angle acquiring unit 1011 calculates a direction vector to indicate the line 1210 from the coordinates of the intersection and the coordinates of the transducer 131, calculates a normal vector at the coordinates of the intersection from the coordinates of the intersection and the shape data, and calculates an angle formed by these vectors using an inner product. Then the relative angle acquiring unit 1011 subtracts 90° from the calculated angle, and determines the absolute value of the result, whereby the relative angle 1220 is acquired. The above step is executed for each transducer 131, and the result is stored in the storage unit 142.

Figure 12A:
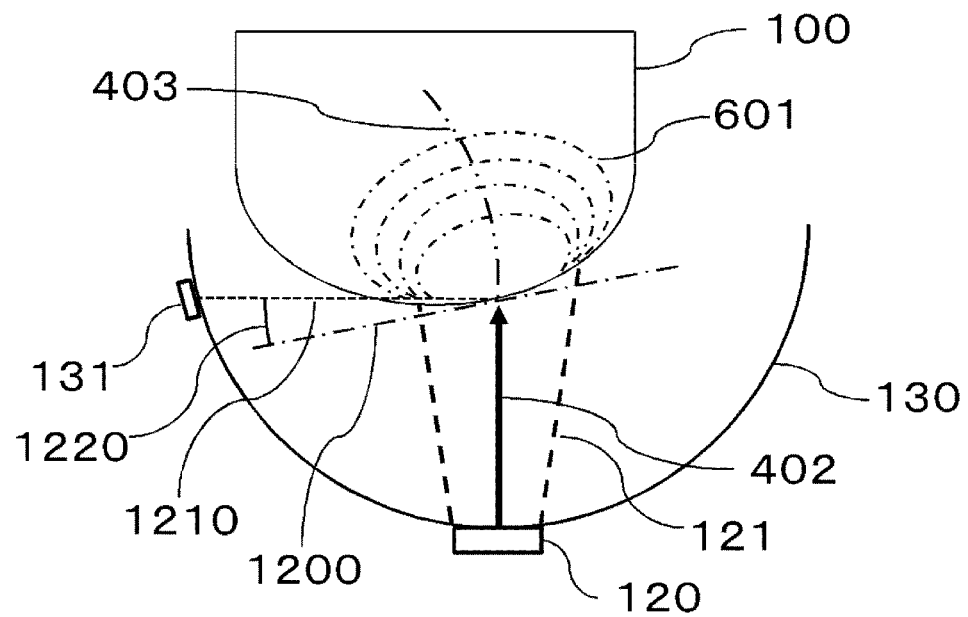
FIG. 12A and FIG. 12B are diagrams depicting a relative angle.
Figure 12B:
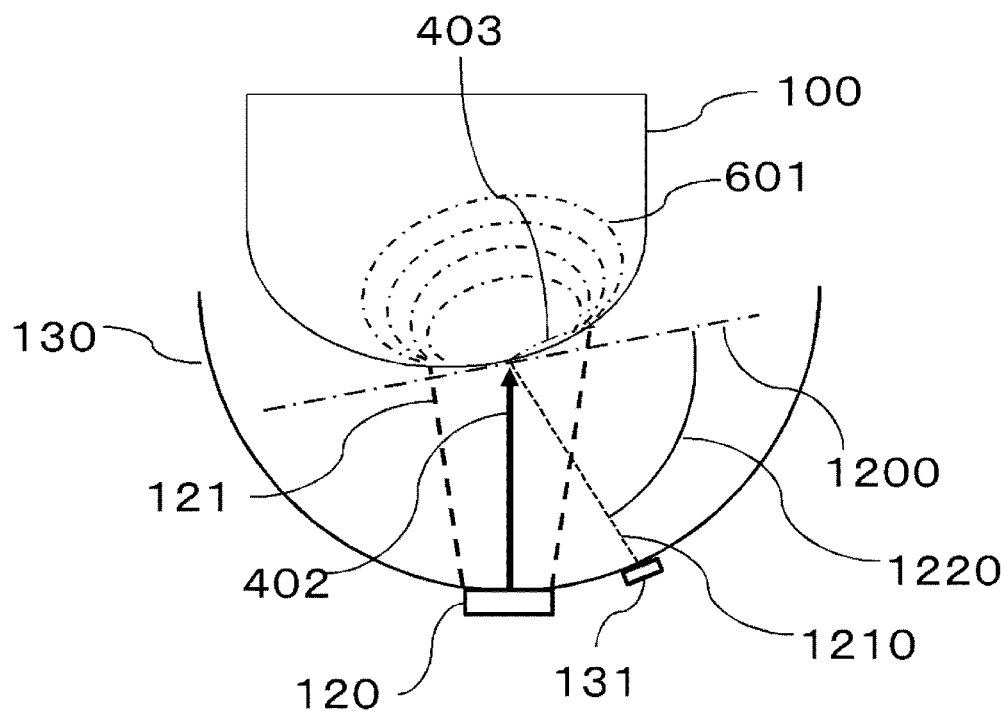

The relationship between the relative angle 1220 and the dispersion of the light intensity distribution on the back projection spherical surface will be described next. If the relative angle 1220 of the transducer 131 is small, as shown in FIG. 12A, the light intensity distribution 601 on the back projection spherical surface 403 decays exponentially, hence dispersion of light intensity is large. If the relative angle 1220 of the transducer 131 is large, on the other hand, as shown in FIG. 12B, the inclination of the light intensity on the back projection spherical surface 403 is gentle, hence the dispersion of the light intensity is small. Therefore, just like the case of the standard deviation of Embodiment 1, the relative angle 1220 can be used as the dispersion index of the light intensity distribution on the back projection spherical surface 403.

(S250: Step of Acquiring Angle Range)

In this step, an angle range to back-project the receiving signal is acquired for each of the transducers 131 using the relative angle acquired in S240. In concrete terms, the angle range is smaller as the relative angle of the transducer is larger. This step is executed by the angle range acquiring unit 1012.

Figure 13A:
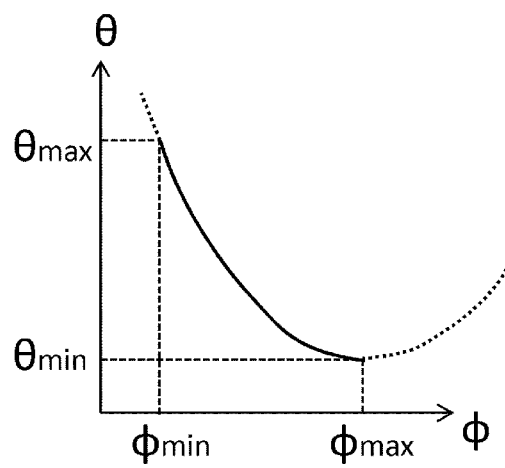
FIG. 13A and FIG. 13B are graphs showing the relationship between the relative angle and the angle range.
Figure 13B:
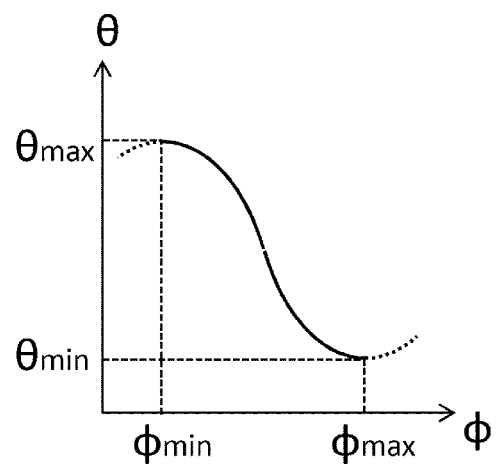

FIG. 13 shows the correspondence of the relative angle $\phi$ and the angle range $\theta$. FIG. 13A is a case when $\theta$ is decayed with respect to $\phi$ using a power function, and FIG. 13B is a case when $\theta$ is decayed with respect to $\phi$ using a cosine function. $\phi_{min}$ and $\phi_{max}$ are the minimum and maximum values of the relative angles of the plurality of transducers 131. $\theta_{min}$ and $\theta_{max}$ are a lower limit and an upper limit of the angle range respectively, and can be set to arbitrary values. For example, a predetermined angle 405 is used for $\theta_{max}$, and an angle sufficiently smaller than the predetermined angle 405 is used for $\theta_{min}$.

This embodiment may be executed for a plurality of times while changing the values of $\theta_{max}$ and $\theta_{min}$, and an image having the best image quality (e.g. contrast) may be selected out of the plurality of acquired images. It is preferable that the correspondence shown in FIG. 13 is stored in the storage unit in a format of a mathematical expression, a table or the like. In this case, if a plurality of correspondences, of which conditions are slightly different from one another, are set, this is convenient for the above mentioned selection. For a concrete correspondence, it is preferable to set predetermined values in advance based on the characteristics of the object, performance of the light source, the optical system and the tranducer, and their positional relationship with the object. Further, it is preferable to set a correspondence unique to the apparatus based on the physical configuration of the apparatus.

FIG. 5 is an example, and any function may be used if the inclination of $\theta$ with respect to $\phi$ is always 0 or less and the inclination becomes negative at least once in the ($\phi_{min}$, $\phi_{max}$) range. Thereby the angle range for back projection becomes smaller as the dispersion of the light intensity of the transducer is greater on the back projection spherical surface. Other functions that can be used are, for example, a linear function, an exponential function and a step function.

The above mentioned processing is performed for each transducer 131, and the angle range to back-project each receiving signal is acquired and stored in the storage unit 142.

(S260: Step of Acquiring Initial Sound Pressure)

Figure 3:
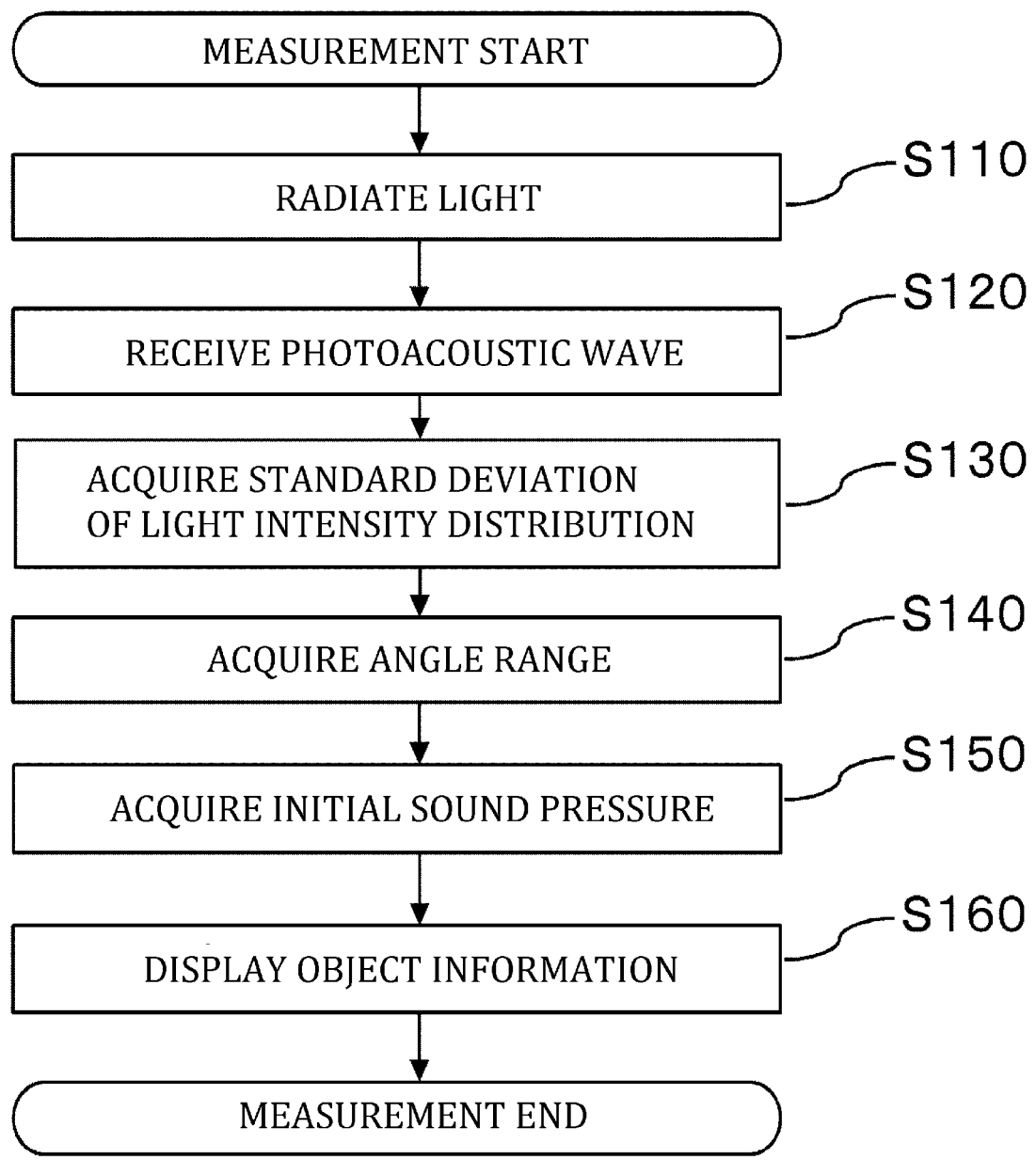
FIG. 3 is a flow chart depicting an object information acquiring method according to Embodiment 1.

This step is basically the same as S150 in FIG. 3. Artifacts in the initial pressure distribution can be reduced by changing the angle range for back projection depending on the transducer based on the relative angle, which is the index of the dispersion of the light intensity distribution. As described above, according to the object information acquiring method of this embodiment, object information which has high quantitativity with reduced artifacts can be acquired with less calculation load.

<Example 2>

Now the result of simulating the object information acquiring method according to Embodiment 2 will be described. Simulation is performed using the same system and conditions as Example 1. To apply Embodiment 2, the power function (degree n=1.6) shown in FIG. 13A is used when the angle range is acquired from the relative angle.

Figure 14:
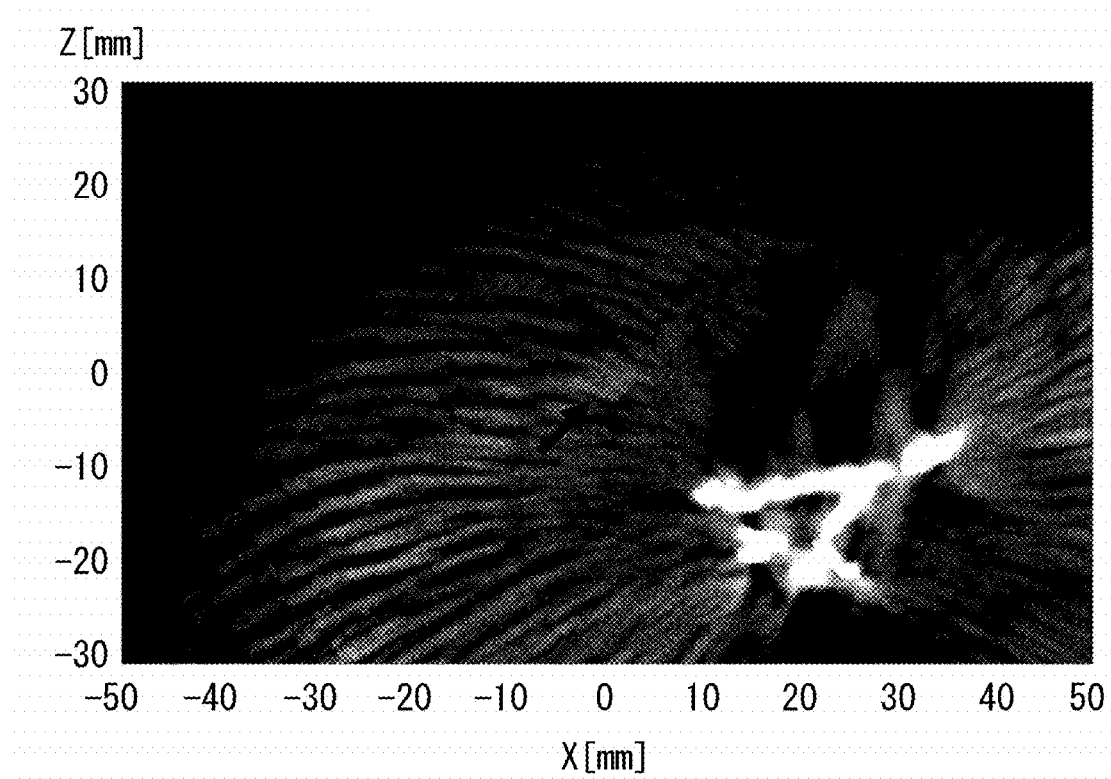
FIG. 14 shows the effect of Example 2.

FIG. 14 shows a result of simulation of the initial sound pressure distribution when the object information acquiring method of Embodiment 2 is applied to the numerical phantom shown in FIG. 8. The conditions of the display is the same as FIG. 9A. Comparing the portion indicated by the arrow mark in FIG. 9A and the portion indicated by the arrow mark in FIG. 14, it is clear that artifacts are reduced in FIG. 14, where the contrast of the light absorber is high and image quality is improved. As described above, object information with reduced artifacts can be acquired by using Embodiment 2.

[Embodiment 3]

In this embodiment, an object information acquiring apparatus that reduces artifacts while maintaining resolution of the initial sound pressure distribution by moving the probe 130 with respect to the object 100 and performing measurement at different positions, will be described. As a rule, a composing element the same as Embodiment 1 and Embodiment 2 is described using the same reference symbol.

<Configuration of Object Information Acquiring Apparatus>

Figure 15:
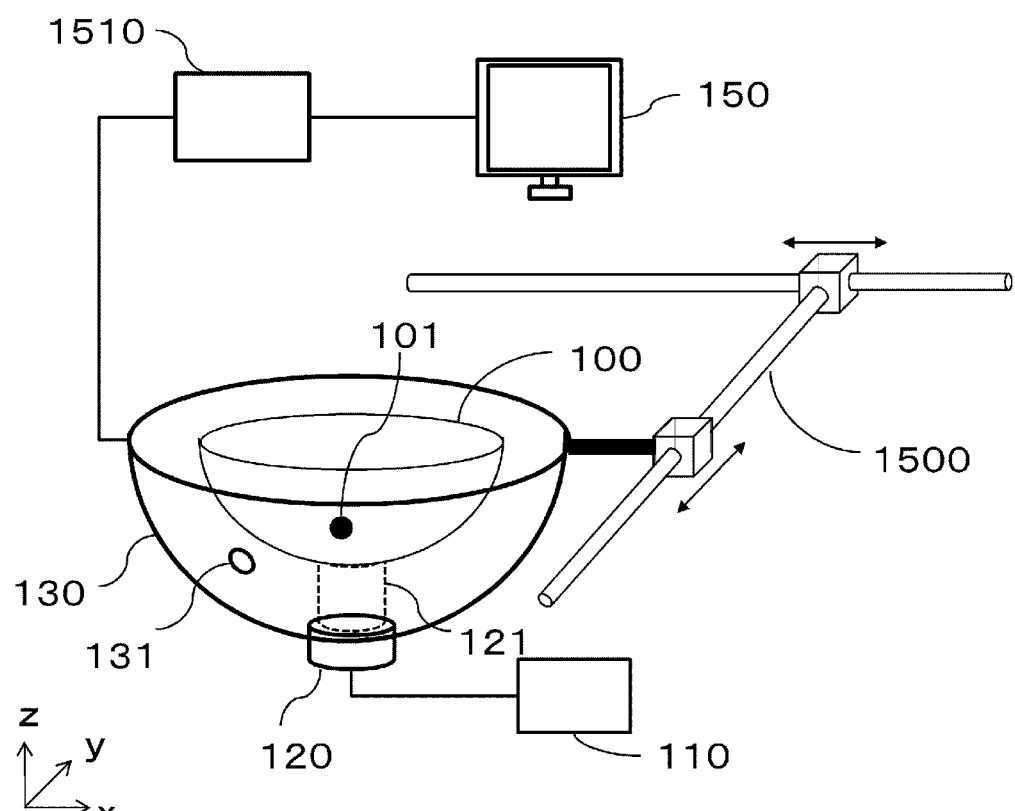
FIG. 15 is a schematic diagram depicting an object information acquiring apparatus according to Embodiment 3.

FIG. 15 is a schematic diagram of the object information acquiring apparatus according to this embodiment.

(Scanning Unit 1500)

Figure 16A:
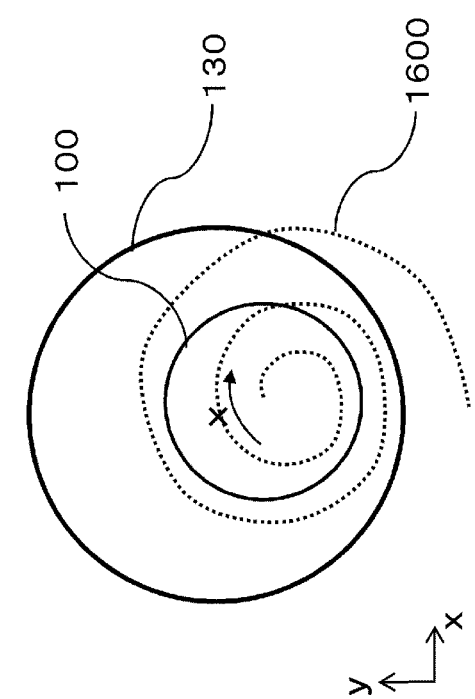
FIG. 16A to FIG. 16C are diagrams depicting scanning loci of the probe.
Figure 16B:
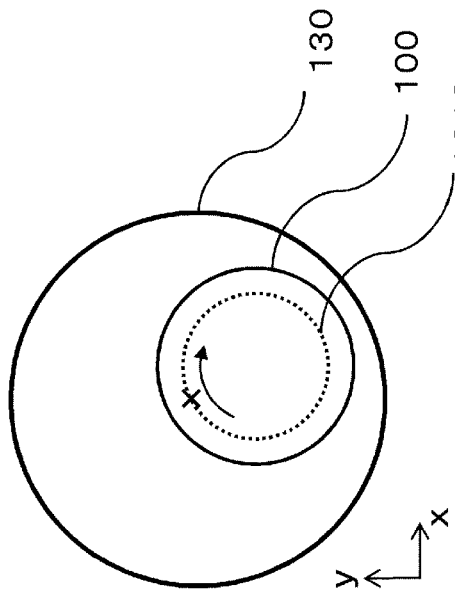
Figure 16C:
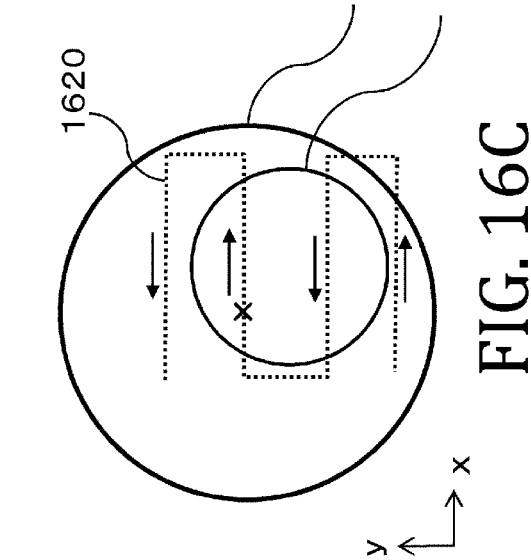

A scanning unit 1500 causes the probe 130 to perform scanning on the object 100 relatively. In FIG. 15, the scanning unit 1500 scans the probe 130 and the optical system 120 on the xy plane. FIG. 16 shows the scanning of the probe 130 on the xy plane, which is seen in the z axis direction. Because of the scanning unit 1500, the probe 130 can scan on the xy plane at various loci, such as a spiral locus 1600 (FIG. 16A), a circular locus 1610 (FIG. 16B) and a linear locus 1620 (FIG. 16C). Light is radiated from the optical system 120 to the object at two or more different points on these loci, so as to generate the photoacoustic wave, whereby the receiving signal is generated by the probe 130. The scanning unit 1500 corresponds to a moving unit according to the present invention.

(Signal Processing Unit 1510)

A storage unit 142 of a signal processing unit 1510 according to this embodiment has a function of performing measurement at a plurality of positions. In other words, the storage unit 142 integrates, for each minimal unit, the initial sound pressure distribution at each measurement position, which the image reconstructing unit 145 generates using the receiving signal acquired at each measurement position, and stores the result. Thereby the integrated initial sound pressure distribution is generated. After the initial sound pressure distribution is integrated at all the scanning positions, the integrated initial sound pressure distribution is averaged by the number of times of integration. Configuration of the storage unit 142 itself may be the same as each embodiment described above. In this case, the above mentioned function can be implemented by the program for controlling the storage unit 142.

<Object Information Acquiring Method>

Figure 17:
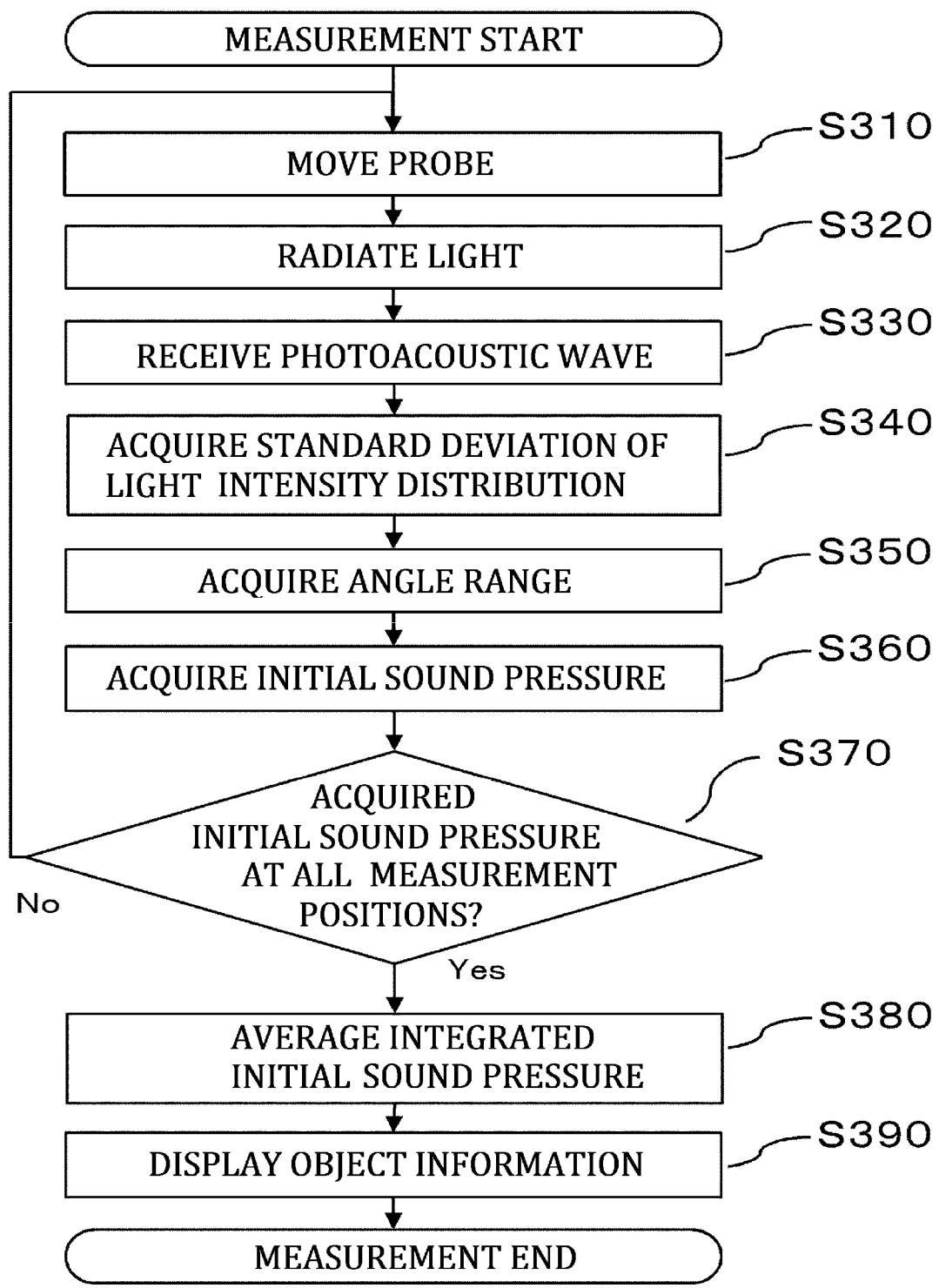
FIG. 17 is a flow chart depicting an object information acquiring method according to Embodiment 3.

Each step of the object information acquiring method according to this embodiment will now be described with reference to FIG. 17. Each step is executed by the control unit 141 which controls operation of each composing element of the object information acquiring apparatus. S320, S330, S340, S350 and S390 in FIG. 17 are the same as S110, S120, S130, S140 and S160 in FIG. 2 respectively, and description thereof is omitted.

(S310: Step of Moving Probe)

In this step, the probe 130 is moved to the next measurement position. This movement is performed by the control unit 141 controlling the scanning unit 1500.

(S360, S370: Steps of Acquiring Initial Sound Pressure at All Measurement Positions)

In these steps, the image reconstructing unit acquires the initial sound pressure distribution from the receiving signal acquired at each measurement position, integrates the value of the initial sound pressure for each minimal unit, and stores the result in the storage unit 142. S310 to S360 are repeated until the receiving signals at all the measurement positions are acquired, and the initial sound pressure distribution at all the measurement positions are integrated and stored in the storage unit 142.

(S380: Step of Averaging Integrated Initial Sound Pressure Distribution)

In this step, the image reconstructing unit determines the initial sound pressure distribution by averaging the integrated initial sound pressure distribution by a number of times of integration. The effect of this embodiment will be described. Here a case of performing the measurement at two different positions is considered. The two measurement positions are assumed to be the position of the probe 130 in FIG. 6 and the position of the probe in FIG. 18.

Figure 18:
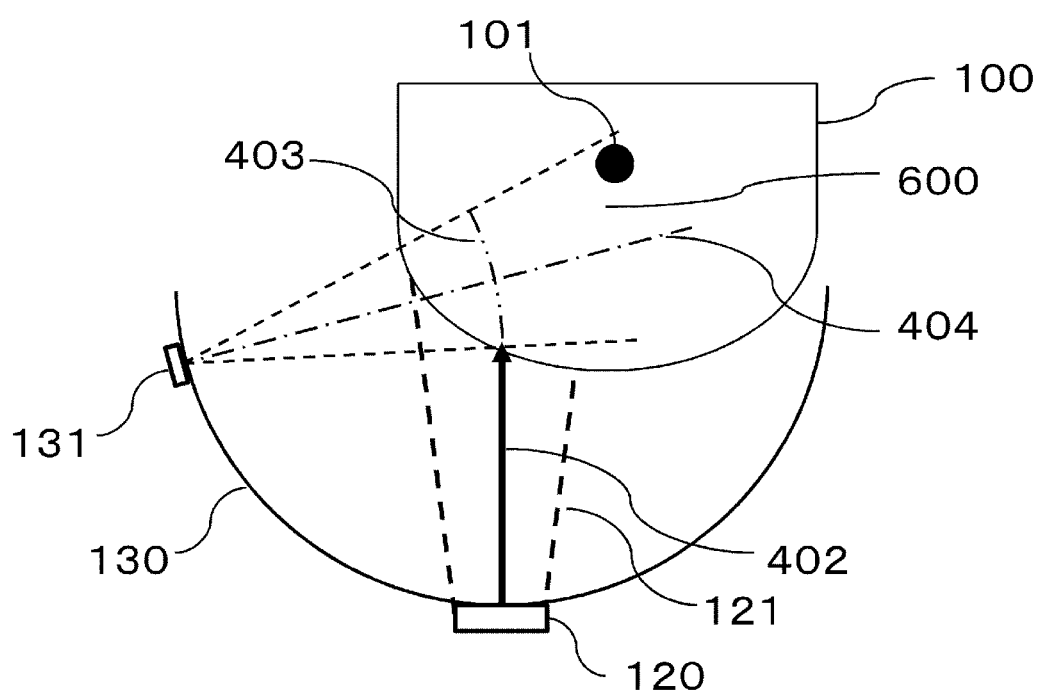
FIG. 18 is a diagram depicting a state when the position of the probe is moved.

In FIG. 18, the light absorber 101 is within the angle range 600, and is also distant from the back projection spherical surface 403, which includes the intersection between the optical axis 402 and the object 100. Therefore if the receiving signal at the measurement position in FIG. 18 is used, the initial sound pressure of the light absorber 101 can be acquired in a low artifact state. In this embodiment, even a transducer 131, of which angle range 600 tends to becomes small, can contribute to the calculation of the initial sound pressure of the light absorber 101, since signals can be received at a plurality of different positions by scanning the probe 130. Thereby the receiving signals are back-projected to the minimal units in the region of the light absorber 101 from various directions, hence the initial sound pressure of the light absorber 101 can be acquired at high resolution.

Furthermore, the operation unit scans not only on the xy plane, but also in the z axis direction, therefore the image quality further improves. In this embodiment as well, the dispersion evaluation method using the relative angle may be used to acquire a similar effect, just like the case of Embodiment 2.

[Embodiment 4]

In this embodiment, the object information acquired by Embodiment 1 or Embodiment 2 and the object information acquired with fixing the angle range are displayed to the operator, whereby the accuracy of the diagnosis is further enhanced. As a rule, a composing element the same as Embodiment 1 or Embodiment 2 is denoted with the same reference symbol, for which description is omitted.

<Configuration of Object Information Acquiring Apparatus>

(Signal Processing Unit)

The image reconstructing unit 145 of the signal processing unit according to this embodiment has a function to acquire the initial sound pressure distribution with fixing the angle range to a predetermined angle 405, in addition to the functions described in each of the above mentioned embodiments.

(Display Unit)

The display unit of this embodiment displays to the operator both the object information acquired by the object information acquiring method of Embodiment 1, and the object information acquired with fixing the angle range to a predetermined angle 405. The display method can be a parallel display where the two object information are displayed in parallel, an alternating display where the two object information are alternately switched between and displayed, and a superimposed display where the two object information are superimposed and displayed.

<Object Information Acquiring Method>

Figure 19:
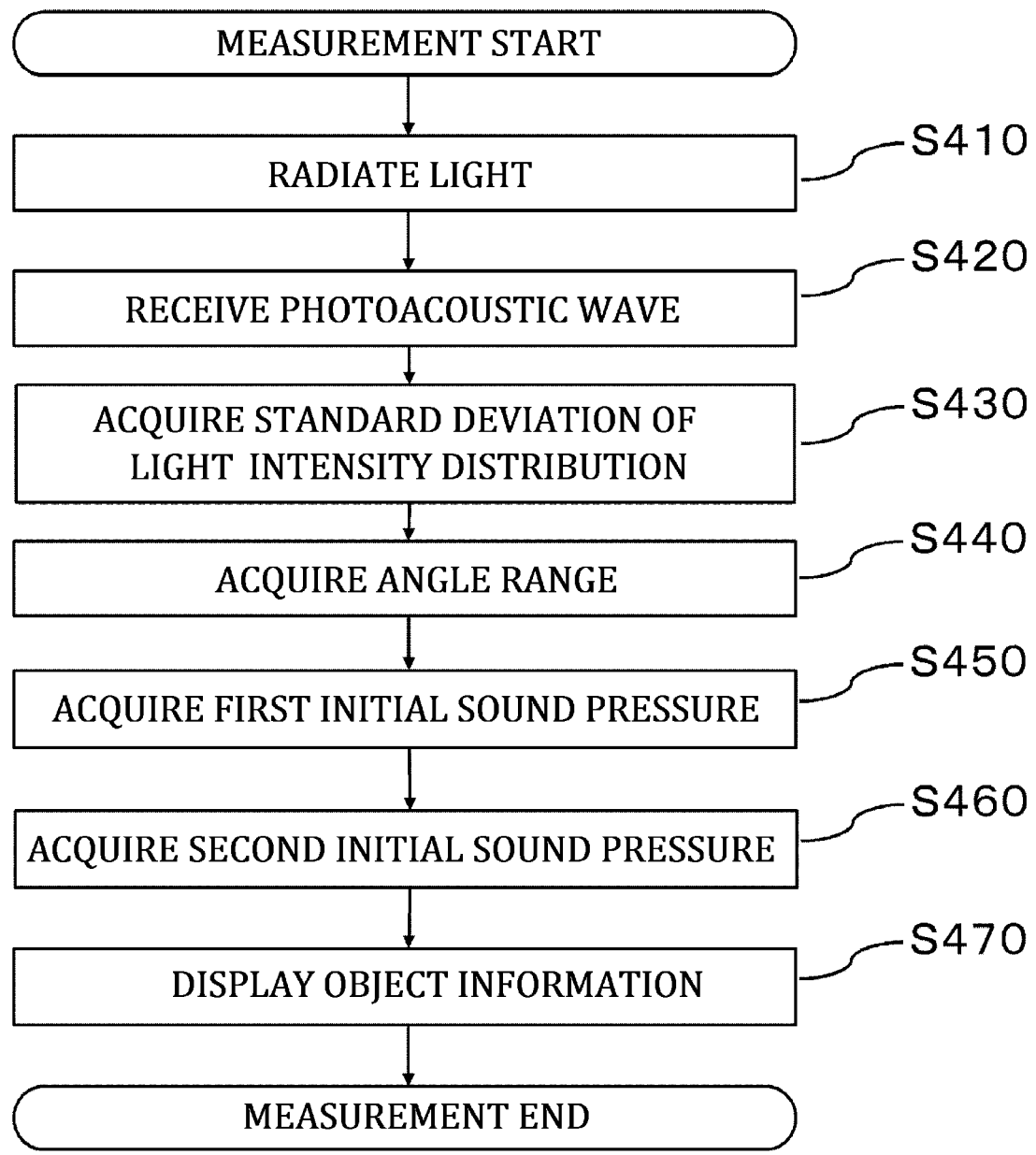
FIG. 19 is a flow chart depicting an object information acquiring method according to Embodiment 4.

Each step of the object information acquiring method according to this embodiment will now be described with reference to FIG. 19. Each step is executed by the control unit 141, which controls operation of each composing element of the object information acquiring apparatus. S410, S420, S430 and S440 in FIG. 19 are the same as S110, S120, S130 and S140 in FIG. 3 respectively, and description thereof is omitted.

(S450: Step of Acquiring First Initial Sound Pressure Distribution)

In this step, the image reconstructing unit stores the initial sound pressure distribution, which is acquired by a step similar to S150 in Embodiment 1, in the storage unit 142 as the first initial sound pressure distribution.

(S460: Step of Acquiring Second Initial Sound Pressure Distribution)

In this step, the image reconstructing unit calculates Expression (1) with fixing the angle range to back-project the receiving signals from all the transducers 131 to a predetermined angle (405 in FIG. 6), whereby the second initial sound pressure distribution is acquired. The acquired second initial sound distribution is stored in the storage unit 142 independently from the first initial sound pressure distribution acquired in S450.

(S470: Step of Displaying Object Information)

In this step, the object information based on the first initial sound pressure distribution and the object information based on the second initial sound pressure distribution are displayed on the display unit.

The effect of this embodiment will be described. In S450, the initial sound pressure distribution, in which artifacts are reduced as described in Embodiment 1 (first initial sound pressure distribution), is acquired. This is the effect of decreasing the angle range for back projection, as shown in 600 in FIG. 6. In this case however, the possibility that a light absorber will exist outside the angle range also increases. On the other hand, in S460, the receiving signals are back-projected in a wide range, as seen in the predetermined angle 405 in FIG. 6A. The receiving signals used in this case are not only the receiving signals originating from the surface of the object having strong light intensity, but also includes receiving signals originating from the light absorber 101. Therefore an initial sound pressure distribution which has high resolution, even if more artifacts are generated (second initial sound pressure distribution), is acquired in S460. By displaying the object information based on the two initial sound pressure distributions which have different characteristics in terms of contrast of an artifact and resolution, the operator can receive auxiliary information from two images, and the accuracy of diagnosis can be improved.

In this embodiment, the object information acquiring method of Embodiment 1 is used to acquire the first initial sound pressure, but a similar effect can be acquired even if a relative angle is used as in Embodiment 2.

As described above, according to the present invention, an object information acquiring apparatus that can reduce the generation of artifacts can be provided. Further, an object information acquiring apparatus that can acquire object information which has high quantitativity with reduced artifacts can be provided.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-259032, filed on Dec. 22, 2014, which is hereby incorporated by reference herein in its entirety.

What is claimed is:

1. An information processing apparatus configured to perform processing by using time-series receiving signals acquired by receiving acoustic waves generated from an object irradiated with the light at a plurality of receiving positions, the apparatus comprising:
   an index acquiring unit configured to acquire, for each of the plurality of receiving positions, a statistical value of the light intensity distribution on the back projection surface as a dispersion index of light intensity distribution on a back projection surface for back-projecting the time-series receiving signals after taking a logarithm of the light intensity distribution on the back projection surface;
   an angle range acquiring unit configured to acquire, for each of the plurality of receiving positions, an angle range in the back projection based on the dispersion index; and
   a characteristic information acquiring unit configured to acquire characteristic information on the interior of the object by back-projecting the plurality of time-series receiving signals in the angle range.

2. The information processing apparatus according to claim 1, wherein the angle range acquiring unit is configured to decrease the angle range as a value of the dispersion index is greater.

3. The information processing apparatus according to claim 1, wherein the angle range acquiring unit is configured to decrease the angle range when a value of the dispersion index exceeds a predetermined threshold.

4. The information processing apparatus according to claim 1, wherein the angle range acquiring unit is configured to acquire the angle range using a function which returns the angle range with respect to the dispersion index and has 0 or less inclination which becomes negative at least once in a range of possible values of the dispersion index.

5. The information processing apparatus according to claim 1, wherein the index acquiring unit is configured to acquire the statistical value on the back projection surface that includes an intersection of an optical axis of the light and the surface of the object.

6. The information processing apparatus according to claim 1, wherein the index acquiring unit is configured to acquire, as the dispersion index, a relative angle formed by a tangential plane at the intersection of the optical axis of the light and the surface of the object and a line connecting the receiving unit for receiving the acoustic waves and the intersection.

7. The information processing apparatus according to claim 1, wherein the index acquiring unit is configured to acquire the dispersion index on a plurality of the back projection surfaces having different radii corresponding to respective signal value of the time-series receiving signals at each timing, and
   the angle range acquiring unit is configured to acquire the angle range for each of the plurality of back projection surfaces.

8. The information processing apparatus according to claim 1, further comprising:
   a light intensity distribution acquiring unit configured to acquire the light intensity distribution by numerical operation or by referring to a table.

9. An object information acquiring apparatus comprising:
   the information processing apparatus according to claim 1;
   an irradiating unit configured to irradiate the object with the light; and
   a receiving unit configured to receive the acoustic waves at the plurality of receiving positions and output the time-series receiving signals corresponding to the plurality of receiving positions respectively.

10. The object information acquiring apparatus according to claim 9, further comprising a scanning unit configured to change a positional relationship between the receiving unit and the object.

11. The object information acquiring apparatus according to claim 10, wherein the characteristic information acquiring unit is configured to acquire the characteristic information using the time-series receiving signals acquired at each position to which the receiving unit has been moved by the scanning unit.

12. An information processing apparatus which performs processing by using time-series receiving signals acquired by receiving acoustic waves generated from an object irradiated with the light at a plurality of receiving positions, the apparatus comprising:
   an index acquiring unit configured to acquire, for each of the plurality of receiving positions, a statistical value of the light intensity distribution on a back projection surface as a dispersion index of light intensity distribution on the back projection surface for back-projecting the time-series receiving signals;
   an angle range acquiring unit configured to acquire, for each of the plurality of receiving positions, an angle range in the back projection based on the dispersion index; and
   a characteristic information acquiring unit configured to acquire characteristic information on the interior of the object by back-projecting the plurality of time-series receiving signals in the angle range,
   wherein the statistical value of the light intensity distribution on a back projection surface includes an intersection of an optical axis of the light and the surface of the object.

13. The information processing apparatus according to claim 12, wherein the angle range acquiring unit is configured to decrease the angle range as a value of the dispersion index is greater.

14. The information processing apparatus according to claim 12, wherein the angle range acquiring unit is configured to decrease the angle range when a value of the dispersion index exceeds a predetermined threshold.

15. The information processing apparatus according to claim 12, wherein the angle range acquiring unit is configured to acquire the angle range using a function which returns the angle range with respect to the dispersion index and has 0 or less inclination which becomes negative at least once in a range of possible values of the dispersion index.

16. The information processing apparatus according to claim 12, wherein the index acquiring unit is configured to acquire the dispersion index on a plurality of the back projection surfaces having different radii corresponding to respective signal value of the time-series receiving signals at each timing, and
   the angle range acquiring unit is configured to acquire the angle range for each of the plurality of back projection surfaces.

17. The information processing apparatus according to claim 12, further comprising:
   a light intensity distribution acquiring unit configured to acquire the light intensity distribution by numerical operation or by referring to a table.

18. An object information acquiring apparatus comprising:
   the information processing apparatus according to claim 12,
   an irradiating unit configured to irradiate the object with the light; and
   a receiving unit configured to receive the acoustic waves at the plurality of receiving positions and output the time-series receiving signals corresponding to the plurality of receiving positions respectively.

19. An information processing apparatus which performs processing by using time-series receiving signals acquired by receiving acoustic waves generated from an object irradiated with the light at a plurality of receiving positions, the apparatus comprising:
   an index acquiring unit configured to acquire, for each of the plurality of receiving positions, a dispersion index of light intensity distribution on a plurality of back projection surfaces having different radii corresponding to respective signal value of the time-series receiving signals at each timing;
   an angle range acquiring unit configured to acquire, for each of the plurality of receiving positions and each of the plurality of back projection surfaces, an angle range in the back projection based on the dispersion index; and
   a characteristic information acquiring unit configured to acquire characteristic information on the interior of the object by back-projecting the plurality of time-series receiving signals in the angle range.

20. The information processing apparatus according to claim 19, wherein the angle range acquiring unit is configured to decrease the angle range as a value of the dispersion index is greater.

21. The information processing apparatus according to claim 19, wherein the angle range acquiring unit is configured to decrease the angle range for each of the plurality of back projection surfaces when a value of the dispersion index exceeds a predetermined threshold.

22. The information processing apparatus according to claim 19, wherein the angle range acquiring unit is configured to acquire the angle range using a function which returns the angle range with respect to the dispersion index and has 0 or less inclination which becomes negative at least once in a range of possible values of the dispersion index.

23. The information processing apparatus according to claim 19, wherein the index acquiring unit is configured to acquire a statistical value of the light intensity distribution on the back projection surface as the dispersion index.

24. The information processing apparatus according to claim 19, further comprising:
   a light intensity distribution acquiring unit configured to acquire the light intensity distribution by numerical operation or by referring to a table.

25. An object information acquiring apparatus comprising:
   the information processing apparatus according to claim 19;
   an irradiating unit configured to irradiate the object with the light; and
   a receiving unit configured to receive the acoustic waves at the plurality of receiving positions and output the time-series receiving signals corresponding to the plurality of receiving positions respectively.

* * * * *